US010561380B2

(12) United States Patent
Sra et al.

(10) Patent No.: US 10,561,380 B2
(45) Date of Patent: Feb. 18, 2020

(54) DETERMINING AND DISPLAYING THE 3D LOCATION AND ORIENTATION OF A CARDIAC-ABLATION BALLOON

(71) Applicant: APN Health, LLC, Pewaukee, WI (US)

(72) Inventors: Jasbir Sra, Pewaukee, WI (US); Shivani Kohut, Fayetteville, NC (US)

(73) Assignee: APN Health, LLC, Pewaukee, WI (US)

( * ) Notice: Subject to any disclaimer, the term of this patent is extended or adjusted under 35 U.S.C. 154(b) by 447 days.

(21) Appl. No.: 15/584,266

(22) Filed: May 2, 2017

(65) Prior Publication Data

US 2018/0317864 A1    Nov. 8, 2018

(51) Int. Cl.
*A61B 6/12* (2006.01)
*A61B 6/00* (2006.01)
(Continued)

(52) U.S. Cl.
CPC ............... *A61B 6/12* (2013.01); *A61B 6/487* (2013.01); *A61B 18/1492* (2013.01); *A61M 25/10* (2013.01); *A61B 6/466* (2013.01); *A61B 6/5288* (2013.01); *A61B 2018/0022* (2013.01); *A61B 2018/00577* (2013.01); *A61B 2018/0212* (2013.01); *A61B 2090/3966* (2016.02); *A61M 2025/1079* (2013.01)

(58) Field of Classification Search
CPC ............... A61B 18/02; A61B 18/1492; A61B 2018/0022; A61B 2018/00351; A61B 2018/00577; A61B 2018/0212; A61B 2034/104; A61B 2090/376; A61B 2090/3966; A61B 6/12; A61B 6/466; A61B 6/487; A61B 6/5288; A61M 2025/1079; A61M 25/10

See application file for complete search history.

(56) References Cited

U.S. PATENT DOCUMENTS

| 7,995,819 B2 | 8/2011 | Vaillant et al. |
| 8,224,432 B2 | 7/2012 | MacAdam et al. |

(Continued)

FOREIGN PATENT DOCUMENTS

| EP | 2689722 | 1/2014 |
| EP | 2848191 | 3/2015 |

(Continued)

*Primary Examiner* — Michael T Rozanski
(74) *Attorney, Agent, or Firm* — Jansson Munger McKinley & Kirby Ltd.

(57) ABSTRACT

A method for generating and displaying a 3D visualization of a cardiac-ablation balloon with a location marker and central catheter portion in a heart, the method using single-plane fluoroscopic images and comprising: placing, inflating and positioning the balloon; capturing a first burst of images from a first angle; capturing a burst of images from a second (different) angle; selecting an image from each burst to minimize cardio-respiratory phase differences therebetween; identifying the location marker in each image; placing first and second orientation markers in two images where the central catheter portion intersects a projected balloon image farthest from the location marker; associating the second-view location and orientation markers in the selected second-view image with the first-view location orientation markers; determining balloon 3D location and orientation of the balloon using the selected images and associated orientation markers; and inserting a balloon model into the 3D visualization for display.

31 Claims, 15 Drawing Sheets

(51) Int. Cl.
*A61B 18/14* (2006.01)
*A61B 18/24* (2006.01)
*A61B 5/0205* (2006.01)
*A61B 5/0456* (2006.01)
*A61M 25/10* (2013.01)
*A61B 18/00* (2006.01)
*A61B 18/02* (2006.01)
*A61B 90/00* (2016.01)

(56) References Cited

U.S. PATENT DOCUMENTS

| | | |
|---|---|---|
| 8,275,452 B2 | 9/2012 | MacAdam et al. |
| 8,306,612 B2 | 11/2012 | MacAdam |
| 8,768,440 B1 | 7/2014 | Brodnick et al. |
| 8,788,024 B1 | 7/2014 | Brodnick et al. |
| 8,812,091 B1 | 8/2014 | Brodnick |
| 8,948,856 B2 | 2/2015 | Brodnick et al. |
| 8,948,857 B2 | 2/2015 | Brodnick |
| 9,186,081 B2 | 11/2015 | Alfonso et al. |
| 9,314,179 B1 | 4/2016 | Brodnick et al. |
| 9,392,951 B2 | 7/2016 | Greenspan et al. |
| 2003/0220555 A1 | 11/2003 | Heigl et al. |
| 2013/0243153 A1 | 9/2013 | Sra et al. |
| 2016/0106336 A1 | 4/2016 | Li et al. |
| 2016/0235383 A1 | 8/2016 | Bar-Tal et al. |
| 2017/0251942 A1 | 9/2017 | Brodnick et al. |

FOREIGN PATENT DOCUMENTS

| | | |
|---|---|---|
| WO | 2015130824 | 9/2015 |
| WO | 2015148470 | 10/2015 |

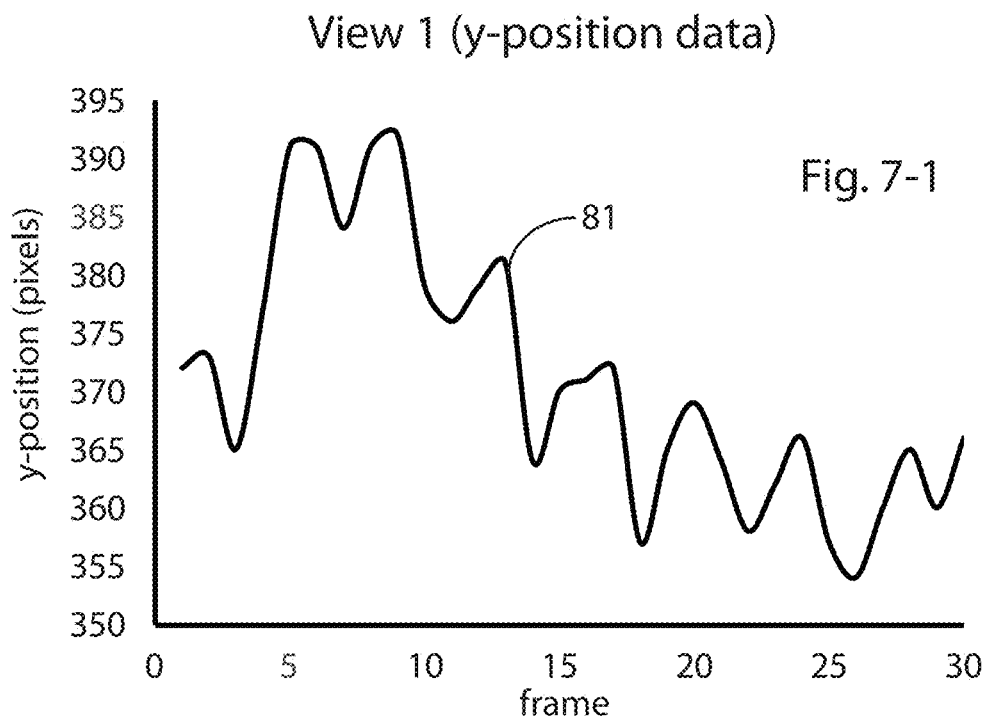
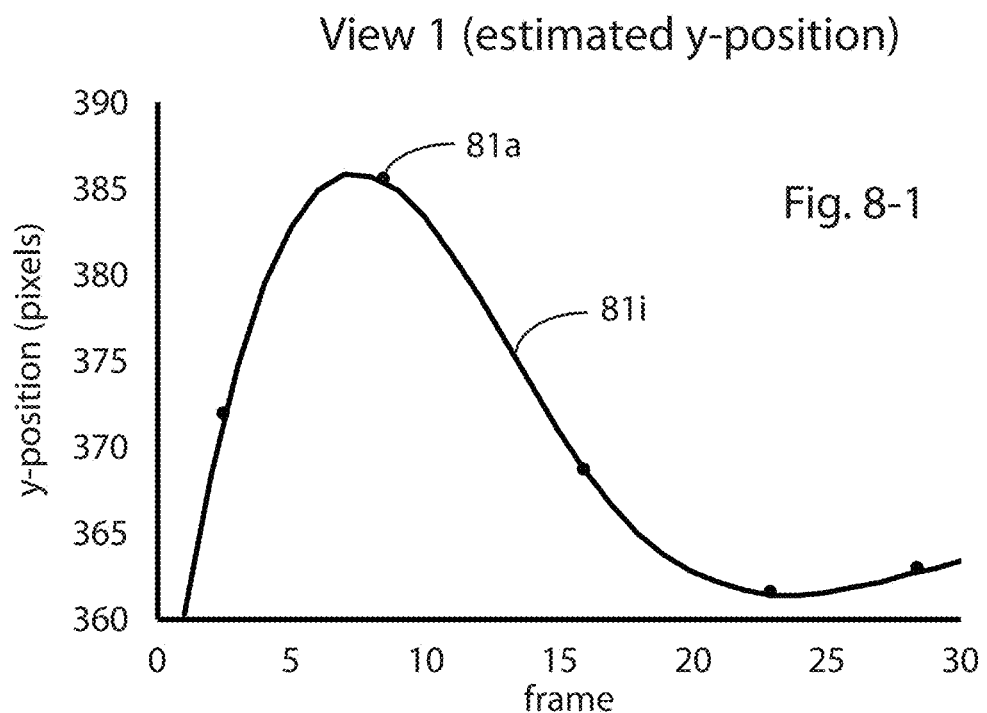

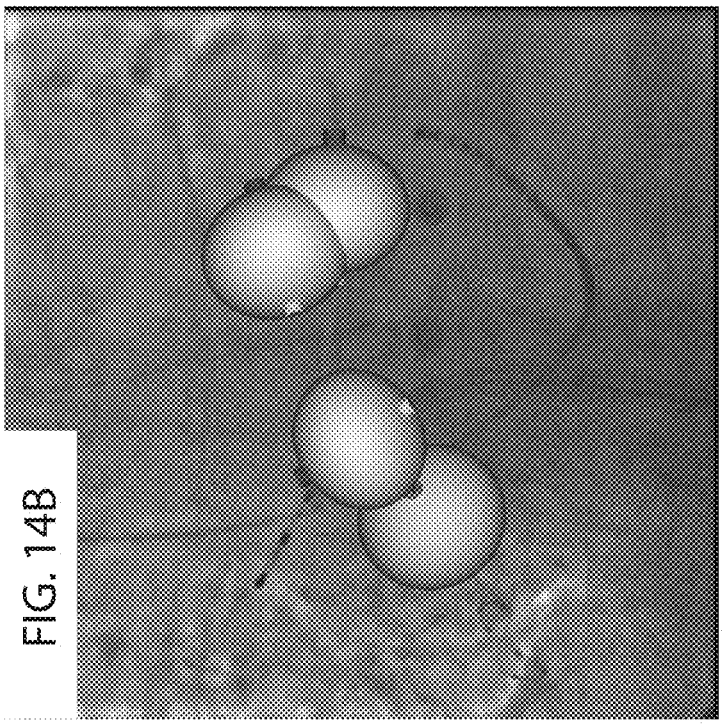
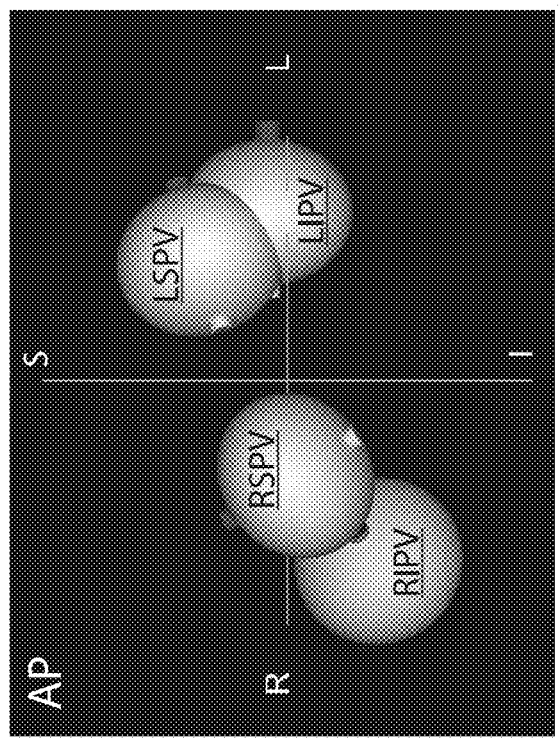
FIG. 14A
FIG. 14B

DETERMINING AND DISPLAYING THE 3D LOCATION AND ORIENTATION OF A CARDIAC-ABLATION BALLOON

FIELD OF THE INVENTION

This invention is related generally to the field of medical fluoroscopy, and more particularly to the area of cardioablation using a balloon catheter within a living heart.

BACKGROUND OF THE INVENTION

In recent years, wide-area ablation of cardiac tissue using balloons has been developed as an alternative to point-by-point ablation procedures. Several types of cardiac-ablation balloon catheters have been introduced. Among these are cryoballoons which use freezing (sometimes referred to as cryo energy) to ablate tissue, radio-frequency hot balloons which use radio-frequency energy for ablation, ultrasonic balloons which deliver focused ultrasonic energy to the tissue, and laser balloons which use light energy as the means of ablation.

The use of cardiac-ablation balloon catheters for the treatment of patients with atrial fibrillation has become an important medical procedure such that it is estimated that in 2016, there were more than 80,000 such procedures worldwide. This common tachyarrhythmia (atrial fibrillation) is often triggered by ectopic foci in and around the pulmonary veins. Prior to the use of cardiac-ablation balloons for this treatment, ablation was carried out using point-by-point ablation strategies in order to electrically isolate the pulmonary veins.

A major shortcoming in the use of cardiac-ablation technology has been that the electrocardiologist performing such procedures has had no good way to visualize after ablation has taken place just where the ablation has been applied. Since most often ablation is done at more than one location in the heart (e.g., there are four pulmonary veins), it would be important and extremely useful to the electrophysiologist to be able to refer visually to the geometry of the entire procedure as it proceeds. The present invention is a method which provides this capability to the physician both during a procedure and after the procedure (by virtue of a stored record).

Some of the technology used in the inventive method disclosed herein involves method steps applicable to a method for rapidly generating a 3D map of a cardiac parameter in a region of a living heart using single-plane fluoroscopic images as disclosed within a co-pending United States Patent Application titled "Rapid 3D Medical Parameter Mapping", application Ser. No. 15/487,245 (herein referred to as Sra et al.), filed on Apr. 13, 2017.

OBJECTS OF THE INVENTION

It is an object of this invention to provide a method that provides a means by which a cardiologist can visualize in three dimensions where a cardiac-ablation balloon has been used to ablate tissue in a living heart after the balloon has been moved away.

Another object of this invention is to provide such visualization using only single-plane fluoroscopic images to provide the data from which the visualization is generated.

Another object of this invention is to provide such visualization in a manner which does not increase the length of time of the cardiac-ablation procedure.

Another object of this invention is to provide such visualization in a form in which it can be stored for later use.

Yet another object of this inventive method is to provide convenient and useful ways for the visualization to be displayed for the cardiologist, including ways in which the cardiologist may interact with the display device to enhance the insight provided.

These and other objects of the invention will be apparent from the following descriptions and from the drawings.

SUMMARY OF THE INVENTION

The present invention is a method for generating and displaying a 3D visualization of a cardiac-ablation balloon in a region of a living heart within a predefined 3D space using single-plane fluoroscopic images. The method comprises the steps of: (1) placing, inflating and positioning the balloon into the region, the balloon having a radio-opaque location marker and central catheter portion; (2) capturing a burst of first-view digitized 2D images of the region from a fluoroscope positioned at a first angle; (3) capturing a burst of second-view digitized 2D images of the region from the fluoroscope positioned at a second angle different from the first angle; (4) selecting first-view and second-view images from the bursts such that the difference between measures of the cardio-respiratory phases of the selected first-view and second-view images is minimized; (5) identifying the location marker in each of the two selected images; (6) placing first and second orientation markers in the selected first-view and second-view images, respectively, where the central catheter portion intersects the projected image of the inflated balloon at a farthest point from the location marker; (7) associating the location marker and the second orientation marker in the selected second-view image with the location marker and first orientation marker in the selected first-view image; (8) determining 3D location and orientation of the balloon in the region using the selected first-view and second-view images; (9) based on the determined location and orientation, inserting a 3D balloon model into the predefined space to generate the 3D visualization; and (10) displaying the 3D visualization on a display device, whereby a user can visualize where cardiac ablation was applied within the region after the balloon has been moved from where the ablation occurred. In some embodiments of the inventive method, the cardiac-ablation balloon uses light energy to ablate cardiac tissue, in some embodiments the balloon uses radio-frequency energy, in some embodiments the balloon uses focused ultrasonic energy, and in some embodiments the balloon uses freezing to ablate cardiac tissue.

In some preferred embodiments, the displaying step includes displaying a projected image of the 3D visualization onto a 2D fluoroscopic image of the region and in some embodiments, the displaying step includes displaying the 3D visualization in 3D rotatable perspective format.

In some preferred embodiments, selecting a first-view image and a second-view image includes determining a cardiac phase and a respiratory phase for each captured first-view and second-view image. In some of these embodiments, selecting the first-view and second-view images includes the steps of (a) identifying candidate images in the first and second bursts of images for which a cardiac-phase criterion and a respiratory-phase criterion are satisfied and (b) selecting a first-view image and a second-view image from the candidate images using a similarity criterion based on the cardiac phase and respiratory phase of the candidate images.

In some highly-preferred embodiments, the cardiac phase of each image is estimated using an R-wave detector to identify R-waves and measure R-wave intervals. In some of these embodiments, the estimate of the cardiac phase of an image is the percentage of time, along the R-wave interval, at which an image was captured, and in some, the cardiac-phase criterion is satisfied if the estimated cardiac phase of an image is between 30% and 80%.

In some highly-preferred embodiments, the respiratory phase of each image in a burst of images is estimated by (a) determining an exhalation/inhalation range from the locations of a radio-opaque object in the images of the burst and (b) determining the percentage along the exhalation/inhalation range of the location of the radio-opaque object in the image. In some of these embodiments, the radio-opaque object is the location marker, and in some, the respiratory-phase criterion is satisfied when the respiratory phase of an image is between 0% and 20% of maximum exhalation.

In some highly-preferred embodiments of the inventive method, the selecting step further includes (a) for each pair of a candidate first-view image $I_i$ and a candidate second-view image $I_j$, computing the sum of the absolute value of the difference between the cardiac phases of images $I_i$ and $I_j$ and the absolute value of the difference between the respiratory phases of images $I_i$ and $I_j$ and (b) selecting the pair of first-view and second-view images for which the sum is the minimum. In some of these embodiments, the cardiac-phase difference and respiratory-phase difference are given relative weights prior to summing.

In highly-preferred embodiments of the inventive method for generating and displaying a 3D visualization of a cardiac-ablation balloon in a region of a living heart within a predefined 3D space using single-plane fluoroscopic images, all but the placing, inflating and positioning steps take place during cardiac ablation.

In some highly-preferred embodiments, determining the 3D location and orientation of the cardiac-ablation balloon includes determining the 3D locations of the location marker and a final orientation marker from the selected first-view and second-view images using back-projection calculations. In some of these embodiments, the fluoroscope includes a detector defining a detector plane and an X-ray source defining a source point, and determining the 3D location and orientation of the cardiac-ablation balloon further comprises: (a) generating a first plane containing three points defined by the location marker and the first orientation marker of the first-view image in the detector plane and the source point; (b) generating a second plane containing three points defined by the location marker and the second orientation marker of the second-view image in the detector plane and the source point; (c) determining the line of intersection of the first and second planes; (d) determining the location of the balloon from the 3D location of the location marker on the line of intersection; and (e) determining the orientation of the balloon from the determined 3D location of the final orientation marker.

In another aspect of the invention, the method comprises: (a) placing, inflating and positioning the balloon, the balloon having a radio-opaque location marker and a radio-opaque central catheter portion; (b) capturing a first-view digitized 2D image of the region from a first fluoroscope positioned at a first angle; (c) capturing a second-view digitized 2D image of the region from a second fluoroscope positioned at a second angle different from the first angle; (d) identifying the location marker in each image; (e) placing first and second orientation markers in the first-view and second-view images, respectively, where the central catheter portion intersects the projected image of the inflated balloon at the farthest point from the location marker; (f) associating the location marker and second orientation marker in the second-view image with the location marker and first orientation marker in the first-view image; (g) determining 3D location and orientation of the balloon in the region using the selected first-view and second-view images; (h) based on the determined location and orientation, inserting a 3D balloon model into the predefined space to generate the 3D visualization; and (i) displaying the 3D visualization on a display device, whereby a user can visualize where cardiac ablation was applied within the region after the balloon has been moved from where the ablation occurred. In some of these embodiments, the first and second fluoroscopes are the same fluoroscope, and the second-view image is captured subsequent to the capture of the first-view image.

In yet another aspect, the invention is a method for generating and displaying a 3D visualization of a cardiac-ablation balloon in a region of a living heart within a predefined 3D space, the balloon having a radio-opaque location marker and a radio-opaque central-catheter portion, the balloon having been placed, inflated and positioned in the region. The method uses single-plane fluoroscopic images and comprises the steps of: (i) capturing a burst of first-view digitized 2D images of the region from a fluoroscope positioned at a first angle; (ii) capturing a burst of second-view digitized 2D images of the region from the fluoroscope positioned at a second angle different from the first angle; (iii) selecting first-view and second-view images from the bursts such that the difference between measures of the cardio-respiratory phases of the selected first-view and second-view images is minimized; (iv) identifying the location marker in each of the two selected images; (v) placing first and second orientation markers in the selected first-view and second-view images, respectively, where the central catheter portion intersects the projected image of the inflated balloon at a farthest point from the location marker; (vi) associating the location marker and the second orientation marker in the selected second-view image with the location marker and first orientation marker in the selected first-view image; (vii) determining 3D location and orientation of the balloon in the region using the selected first-view and second-view images; (viii) based on the determined location and orientation, inserting a 3D balloon model into the predefined space to generate the 3D visualization; and (ix) displaying the 3D visualization on a display device, whereby a user can visualize where cardiac ablation was applied within the region after the balloon has been moved from where the ablation occurred.

The terms "image" and "frame" are used interchangeably herein and unless otherwise noted, refer to sets of digitized data captured from a conventional fluoroscope. The images or frames are two-dimensional arrays of pixels (picture elements), each pixel having an associated image-intensity value.

The terms "X-ray" and "fluoroscopic" are used interchangeably herein.

The term "burst of images" as used herein refers to a set of sequential fluoroscopic images captured over a period of time, the frequency of which is typically determined by the frame-rate setting of the fluoroscope.

The terms "location" and "position" may be used interchangeably herein to refer to the 3D coordinates of an object such as a radio-opaque marker.

The term "exhalation/inhalation range" as used herein refers to the distance between the extremal 2D positions of a radio-opaque object as it moves from image-to-image within a sequence of images.

The term "cardio-respiratory phase" as used herein refers to the phase of combined cardiac and respiratory motions. Therefore, as used herein, minimizing the difference between the cardio-respiratory phases of two images may also include minimizing a combination of measures of both cardiac phase and respiratory phase.

The terms "method step," "method element," and "functional element" or other similar terms may be used interchangeably herein to refer to portions of the inventive method.

The term "3D balloon model" as used herein refers to a three-dimensional computer image of a cardiac-ablation balloon which includes shape and dimensional information corresponding to an actual cardiac-ablation balloon device. The shape and dimensional information may be customizable such that a "3D balloon model" is adaptable to represent more than one specific cardiac-ablation balloon device. The cardiologist may also adjust the color, opacity, and shading of the 3D model in order to enhance visualization.

BRIEF DESCRIPTION OF THE DRAWINGS

The present invention uses two X-ray images from different angles, View 1 and View 2. In the drawings, when there are corresponding figures for the two views, the numbering convention used herein is that such two-view figures are numbered N-1 and N-2 to indicate that figures relate to View 1 and View 2, respectively.

(FIGS. 3A-3D are used by permission from Medtronic Inc., Minneapolis, Minn.) FIG. 3A shows an uninflated cryoballoon in a left atrium of a heart.

FIG. 3B shows the inflated cryoballoon prior to positioning for a cryoablation procedure.

FIG. 3C shows the inflated cryoballoon in position for cryoablation at the antrum of a pulmonary vein.

FIG. 3D shows the uninflated cryoballoon after ablation.

FIGS. 4-1 and 4-2 are representative X-ray images of a patient's chest in AP (anterior/posterior) and LAO (left anterior oblique) positions, respectively, with a cardiac-ablation balloon, in this case a cryoballoon, in position in a patient. Each of the two images is one image from a burst of images from a first angle (View 1) and one image from a burst of images from a second angle (View 2), respectively.

FIGS. 7-1 and 7-2 are plots of exemplary y-position data for the cardiac-ablation balloon (for location marker 71 in the images of FIGS. 4-1 and 4-2) for thirty (30) frames of a View 1 burst and thirty (30) frames of a View 2 burst, respectively. Note that FIGS. 7-1 and 7-2 are paired with FIGS. 8-1 and 8-2, respectively, and are therefore on different pages, as are FIGS. 8-1 and 8-2.

FIGS. 8-1 and 8-2 are plots of the y-position data of FIGS. 7-1 and 7-2, respectively, which has been smoothed and interpolated to generate an estimate of respiratory phase for each image.

FIGS. 9-1 and 10-1 are plots of the respiratory and cardiac phases for each of the thirty View 1 frames and thirty View 2 frames, respectively. The values of both the cardiac phase and respiratory phase have been normalized onto 0-1 scales. Note that FIGS. 9-1 and 9-2 are paired with FIGS. 10-1 and 10-2, respectively, and are therefore on different pages, as are FIGS. 10-1 and 10-2.

FIGS. 9-2 and 10-2 are plots of the respiratory and cardiac phases for View 1 and View 2 frames, respectively. In each such figure, frames which satisfy a cardiac-phase criterion are plotted, and frames which satisfy a respiratory-phase criterion are also plotted, FIG. 9-2 for View 1 images and FIG. 10-2 for View 2 images. Such frames illustrate the determination of sets of candidate View 1 and View 2 frames for final selection as a pair of images from which to determine the 3D location of the cardiac-ablation balloon using back-projection calculations.

FIG. 13A shows an anterior/posterior view.

FIG. 13B shows a left lateral view.

FIG. 13B shows a right lateral view.

FIG. 13B shows a roof view.

FIG. 14A is the same anterior/posterior view as FIG. 13A, placed next to FIG. 14B for convenience.

FIG. 14B is a representative X-ray image on which an overlay of the 3D perspective image of FIG. 14A has been placed. The opacity of the overlay image is 100%. The X-ray image in FIG. 14B is slightly different from the X-ray image of FIG. 4-1; the X-ray image was taken after all four ablation positions were applied and after the table of the fluoroscopic system had been translated to the right.

DETAILED DESCRIPTION OF PREFERRED EMBODIMENTS

Figure 1:
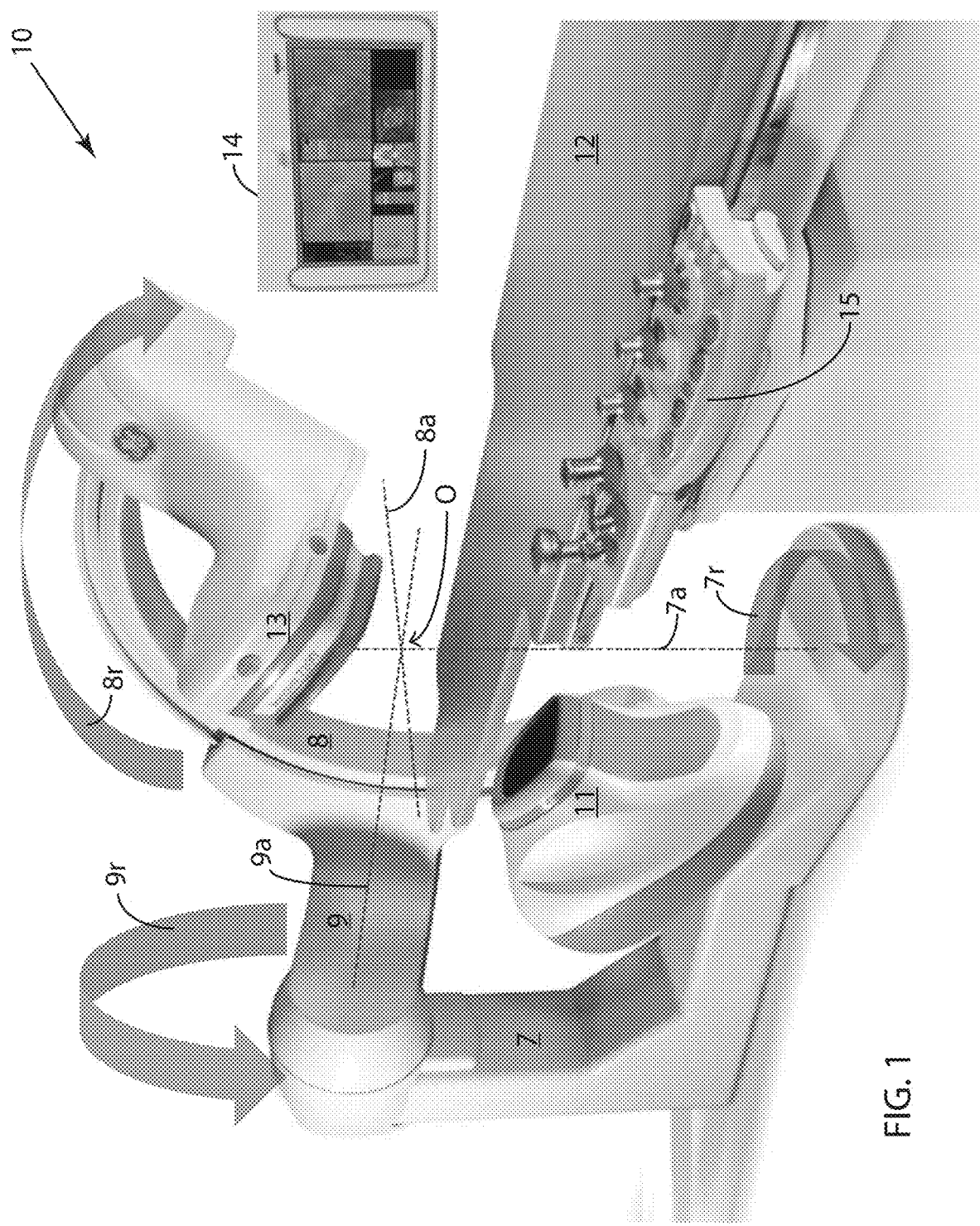
FIG. 1 is an illustration of an exemplary conventional X-ray machine (fluoroscope). The exemplary machine shown in FIG. 1 is a GE Innova 2100 system.

FIG. 1 illustrates an exemplary conventional fluoroscopic system 10 used to acquire 2D fluoroscopic image data. The imaging process for conventional fluoroscopy involves an X-ray source 11 which sends an X-ray beam through a patient (not shown) on a table 12. An X-ray detector 13, which may be a flat-panel detector or an image intensifier/video camera assembly, receives the X-rays transmitted through the patient and converts the X-ray energy into an image.

X-ray source 11 and X-ray detector 13 are mounted on opposite ends of a C-arm 8. Detector 13 may perform the conversion using an X-ray detection layer that either produces light or releases electrons when stimulated by X-rays, and a light-to-electron conversion layer, e.g., photodiodes or electron collection layer, as appropriate, in which an electrical charge signal proportional to X-ray signal intensity in each picture element (pixel) is collected. Analog-to-digital conversion then produces a digital image. Whatever type of X-ray detector 13 is employed, the resulting digital image is then processed, possibly stored, and displayed on a screen 14. A control panel is shown at 15. Images may then be displayed on a computer display 14.

Figure 2:
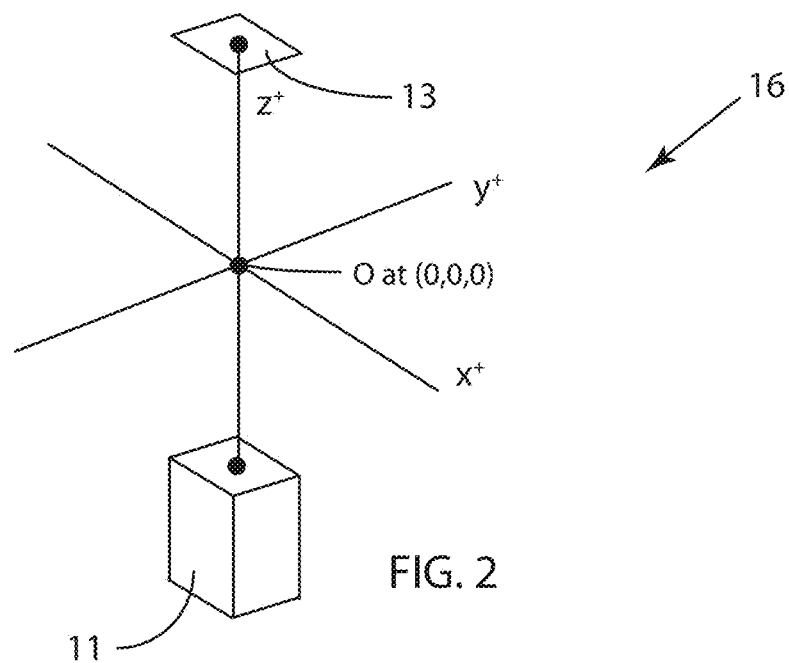
FIG. 2 illustrates an exemplary set of axes which define the 3D coordinates of a procedural fluoroscopic suite. Each element of the suite has a position which can be described by coordinates in this coordinate system. The positive direction of each axis is indicated.

FIG. 2 illustrates an exemplary coordinate system for fluoroscopic system 10. The three axes are shown by the solid lines in FIG. 2. The z-axis is defined from X-ray source 11 to the center of X-ray detector 13 with the X-ray beam vertical and perpendicular to table 12 (the AP position—anterior/posterior position). The positive ($z^+$) direction is defined by the patient's chest (anterior) with $z^-$ as the patient's back (posterior). X-ray table 12 defines an x-axis and a y-axis. The y-axis is parallel to the table with the positive direction ($y^+$) being toward the patient's head (superior). The x-axis is perpendicular to both the y-axis and the z-axis with the positive direction ($x^+$) being to the patient's left. The intersection of the axes is at an origin O, at (0,0,0) of the 3D space defined by axes x, y and z. Control panel 15 is configured to translate the patient along all three of the axes (three translational degrees-of-freedom) as defined above.

As shown in FIG. 1, fluoroscopic system 10 is also configured to rotate around three axes 7a, 8a, 9a (indicated by dotted lines) as a further means to permit the desired positioning of the patient in the field-of-view of the fluoroscopic system 10 and to provide adequate room for medical personnel to perform the desired procedure. In fluoroscopic system 10, origin O is also the center-of-rotation of these three rotational degrees-of-freedom, i.e., the isocenter (center-of-rotation of the X-ray beam central ray) of fluoroscopic system 10. Fluoroscopic system 10 includes a base 7 which is able to rotate on the floor around axis 7a, C-arm 8 which is able to rotate around axis 8a, and an L-arm 9 which is able to rotate around axis 9a. Arrows 7r, 8r and 9r indicate the motion possible with these three rotational degrees-of-freedom.

Note that the three axes x,y,z which define the coordinate system within fluoroscopic system 10 are not necessarily the same as axes 7a,8a,9a since rotations around such axes change the relative positions of theses axes with respect to axes x,y,z. Of course, coordinate systems are relative, and other coordinate systems may be used; the exemplary set of axes described above is not intended to be limiting. Also, not all fluoroscopic systems are configured with all of the translational and rotational degrees-of-freedom which are described in exemplary fluoroscopic system 10, and such set of degrees-of-freedom is not intended to be limiting.

FIGS. 3A through 3D are illustrations of a cardiac-ablation balloon 20 in a region of a living heart. In this case, cardiac-ablation balloon 20 is a cryoballoon. In this sequence of illustrations, cryoballoon 20 (also 20u for uninflated and 20i for inflated) is being placed, inflated and positioned in a left atrium 21 of a living heart for a cryoablation procedure. Cryoballoon 20 is a cardiac instrument which also includes a radio-opaque central catheter 20c and a location marker (not visible in the illustrations of FIGS. 3A-3D).

Figure 3A:
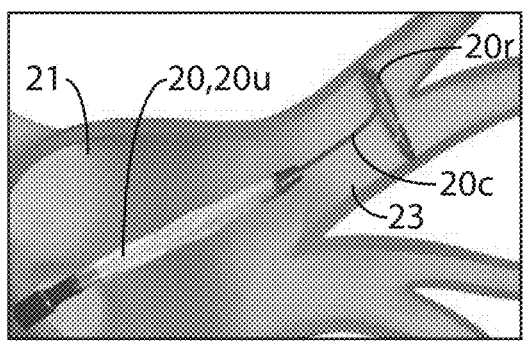
FIGS. 3A through 3D are illustrations of a cardiac-ablation balloon, in this case a cryoballoon, placed in a living heart.

FIG. 3A shows uninflated cryoballoon 20u in left atrium 21. Central catheter 20c includes an end which in FIGS. 3A-3D is a ring-shaped end 20r shown in a pulmonary vein 23.

Figure 3B:
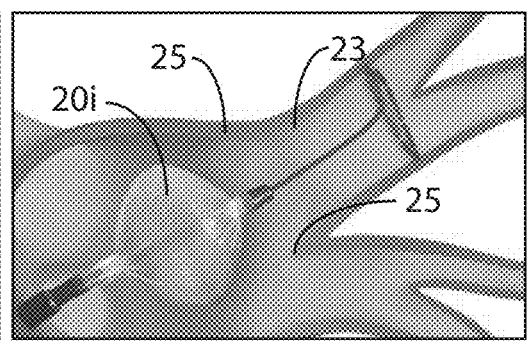

FIG. 3B shows inflated cryoballoon 20i prior to positioning for the cryoablation procedure at the antrum 25 (entrance) of a pulmonary vein 23. (Antrum 25 is indicated by two instances of reference number 25.)

Figure 3C:
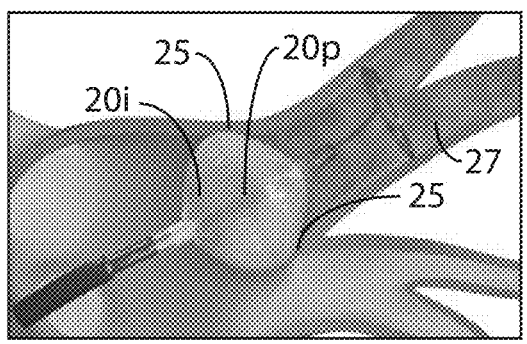

FIG. 3C shows inflated cryoballoon 20i in position at antrum 25 of pulmonary vein 23 for cryoablation. The difference in shading in pulmonary vein 23 to the right of cryoballoon 20i illustrates that prior to cryoablation, fluoroscopic contrast dye 27 is released from the catheter in order to verify that cryoballoon 20i has fully occluded pulmonary vein 23 at antrum 25. After such verification, cardiac tissue is ablated where it is in contact with cryoballoon 20i, forming a circumferential lesion at the desired location in the heart.

Figure 3D:
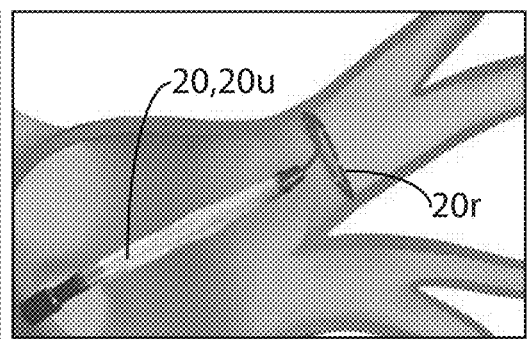

FIG. 3D shows uninflated cryoballoon 20u after the ablation procedure. Ring-shaped end 20r of the catheter includes a plurality of electrodes which are used post-ablation as a mapping catheter to verify the efficacy of the cryoablation procedure.

The inventive method involves the use of one or more programmable computers to carry out the image processing, signal processing and other computational steps involved. In addition, apparatus to sense cardiac rhythm, such as an R-wave detector with its associated electrodes, may be required to supply a signal from which the cardiac phase of the single-plane fluoroscopic images may be derived.

Figures 1, 4:
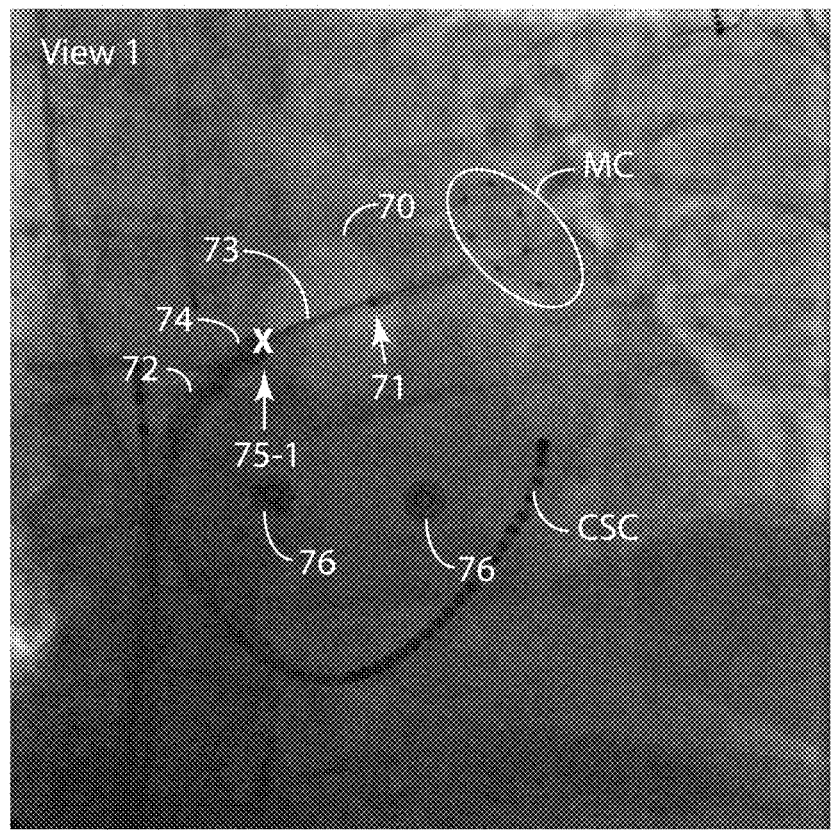
Figures 2, 4:
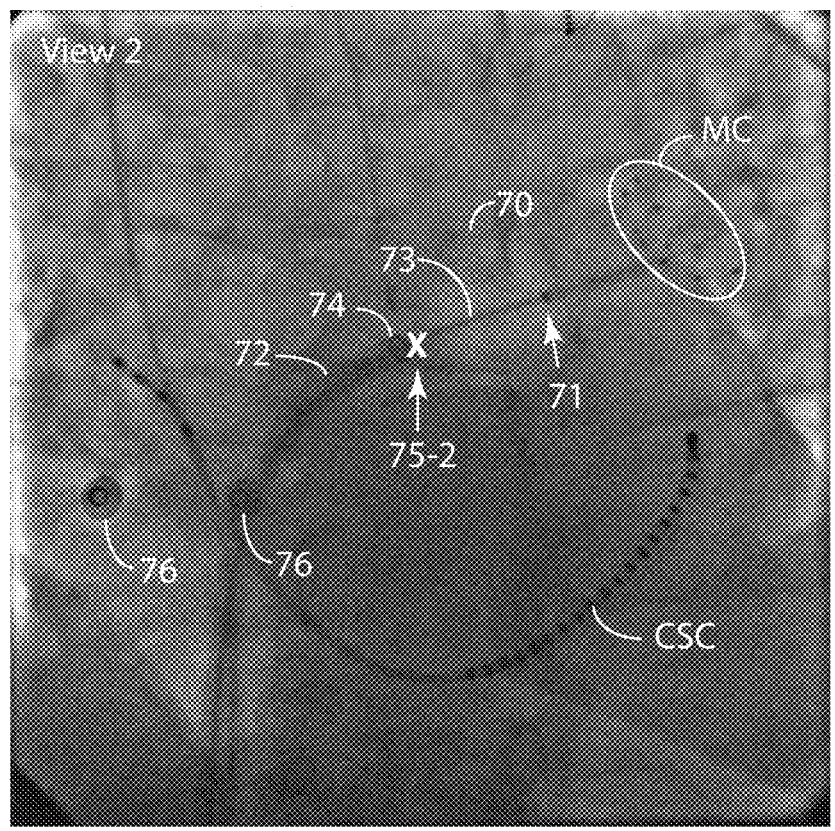

FIGS. 4-1 and 4-2 are representative X-ray images of a patient's chest in AP and LAO 20 (20° to the left) positions, respectively, with a cardiac-ablation balloon 70, in this case a cryoballoon 70 (as part of cardiac catheter 72), in position in a patient. Each of the two images is one image from a burst of images from a first angle (View 1) and one image from a burst of images from a second angle (View 2), respectively. In fact, the pair of images shown in FIGS. 4-1 and 4-2 are images which have been selected as the best pair in the example data used for the selection as described by method steps 31 through 51 in the method embodiment 30 shown in FIG. 5A, described later.

Cryoballoon 70 includes a radio-opaque location marker 71 and a radio-opaque central catheter portion 73 as indicated in FIGS. 4-1 and 4-2. These figures also illustrate two orientation markers 75-1 and 75-2, one in each of the View 1 and View 2 images, respectively, which are digitally placed at the intersection of the image of central catheter portion 73 and cryoballoon 70 at the point farthest from location marker 71 where such intersection occurs. Orientation markers 75-1 and 75-2 are also referred to herein as first and second orientation markers, respectively. The placement of orientation markers 75-1 and 75-2 may occur through manual interaction by a user with the computer system on which the steps of the method have been programmed, through the use of a computer pointing device. The 2D coordinates of orientation markers 75-1 and 75-2 are then captured digitally by the computer system; the 2D coordinates are in detector plane 13.

In this example, location marker 71 is a radio-opaque object near but not at the distal end of cryoballoon 70. In the example presented, location marker 71 is about 5 mm inward from the distal end. Other cardiac-ablation balloons may have different detailed structure but for the application of the inventive method presented herein, a radio-opaque object in a known dimensional relationship with the cardiac-ablation balloon must be available as a location marker.

As can be appreciated from FIGS. 4-1 and 4-2, cryoballoon 70 is less opaque than the surrounding portion of the X-ray images, and thus the visibility of cryoballoon 70 in these X-ray images is quite limited except for location marker 71 and central catheter portion 73, although typically the desired intersection point can be found. This is due to the fact that in an inflated state, cryoballoon 70 contains gas which is less radio-opaque than the blood the gas has displaced, thereby enabling the cardiologist to place orientation markers 75-1 and 75-2.

FIGS. 4-1 and 4-2 also show a radio-opaque ring 74 at the end of the shaft of the catheter 72. The need for placing orientation markers 75-1 and 75-2 in the View 1 and View 2 images comes about since the distance between ring 74 and balloon 70 can vary. The location of ring 74 does not provide accurate information about the location of cryoballoon 70. FIGS. 4-1 and 4-2 also show central catheter portion 73 as being straight. Central catheter portion 73 is the only rigid portion of catheter 72, and the distance between location marker 71 and the opposite end of cryoballoon 70 along central catheter portion 73 is a known distance and does not necessarily extend to ring 74. Thus, this information (locations of location marker 71 and orientation markers 75-1 and 75-2 within the View 1 and View 2 images) is sufficient to enable determination of the 3D location and orientation of cryoballoon 70 from View 1 and View 2 images.

Also shown in FIGS. 4-1 and 4-2 are a coronary sinus catheter CSC and a mapping catheter MC (as well as least one other cardiac catheter). Mapping catheter MC is similar to what was referred to as ring-shaped end 20r (and a mapping catheter) in the illustrated drawings of FIGS. 3A through 3D. In the X-ray images of FIGS. 4-1 and 4-2, mapping catheter MC is not ring-shaped (i.e., in a single plane) but the electrodes of mapping catheter MC are generally oriented in a spiral fashion. The invention disclosed in the aforementioned co-pending Sra et al. application can be used in conjunction with the present invention to create cardiac-parameter maps as necessary contemporaneously with determining the 3D location and orientation of cardiac-ablation balloon 70.

Figure 5A:
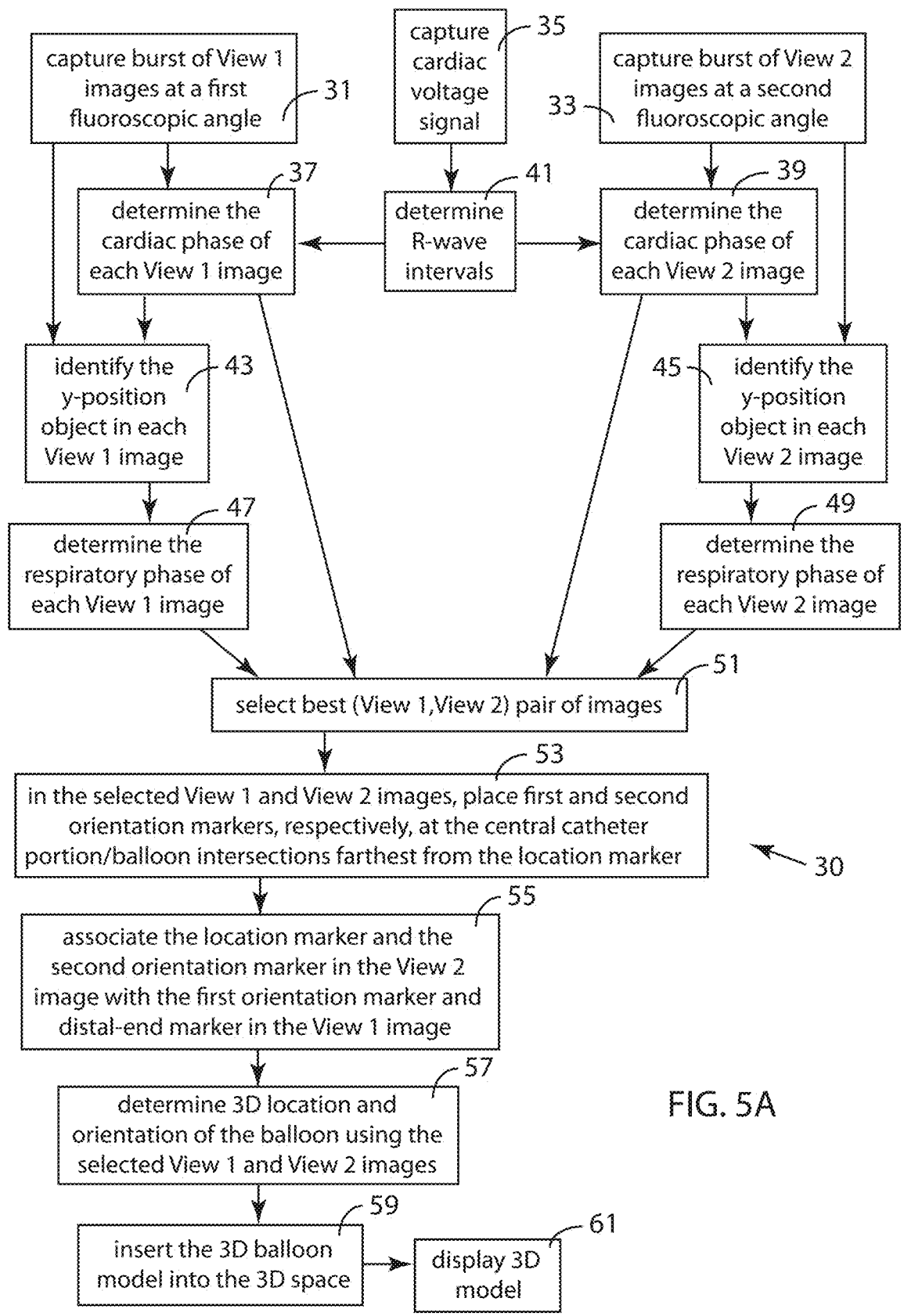
FIG. 5A is a schematic block diagram illustrating an embodiment of the inventive method for generating and displaying a model of a cardiac-ablation balloon in a region of a living heart using single-plane fluoroscopic images.

FIG. 5A is a schematic block diagram illustrating an embodiment 30 of the inventive method for generating and displaying a model of a cardiac-ablation balloon in a region of a living heart using single-plane fluoroscopic images. Method embodiment 30 uses single-plane fluoroscopic images taken from two different angles (View 1 and View 2) in order to enable determination of the 3D location of a cardiac-ablation balloon 70 within predefined coordinates as set forth in FIG. 2.

View 1 and View 2 images may be captured sequentially (with a single fluoroscope set at a first angle and then subsequently at a second angle) or simultaneously (with first and second fluoroscopes). In embodiment 30, a single fluoroscope is used first to capture a burst of View 1 images in method step 31 and subsequently to capture a burst of View 2 images (at a second angle, different from the first angle) in method step 33. (In the example which follows, the frame rate of the fluoroscope is 7.5 frames/second.) The time period of the bursts should be long enough to incorporate at least one full respiratory cycle.

In method step 35, a cardiac voltage signal is captured from which R-wave intervals may be determined in method step 41. Functional elements 37 and 39 use the R-wave data from step 41 to determine a cardiac phase for each View 1 image (step 37) and View 2 image (step 39). In the inventive method, cardiac phase and respiratory phase information are utilized to select the best View 1 and View 2 images for 3D location determination. Since patient motion during a cardiac procedure is primarily caused by cardiac and respiratory activity, in order for sequential View 1 and View 2 images to be used for a calculation which ideally employs image data taken at the same instant in time, selecting the best or optimal View 1 and View 2 images involves finding the pair of images for which a combination of differences in both motion phases is a minimum. Thus, method step 37 and 39 determine cardiac phase information for each View 1 and View 2 images, respectively.

Figure 6:
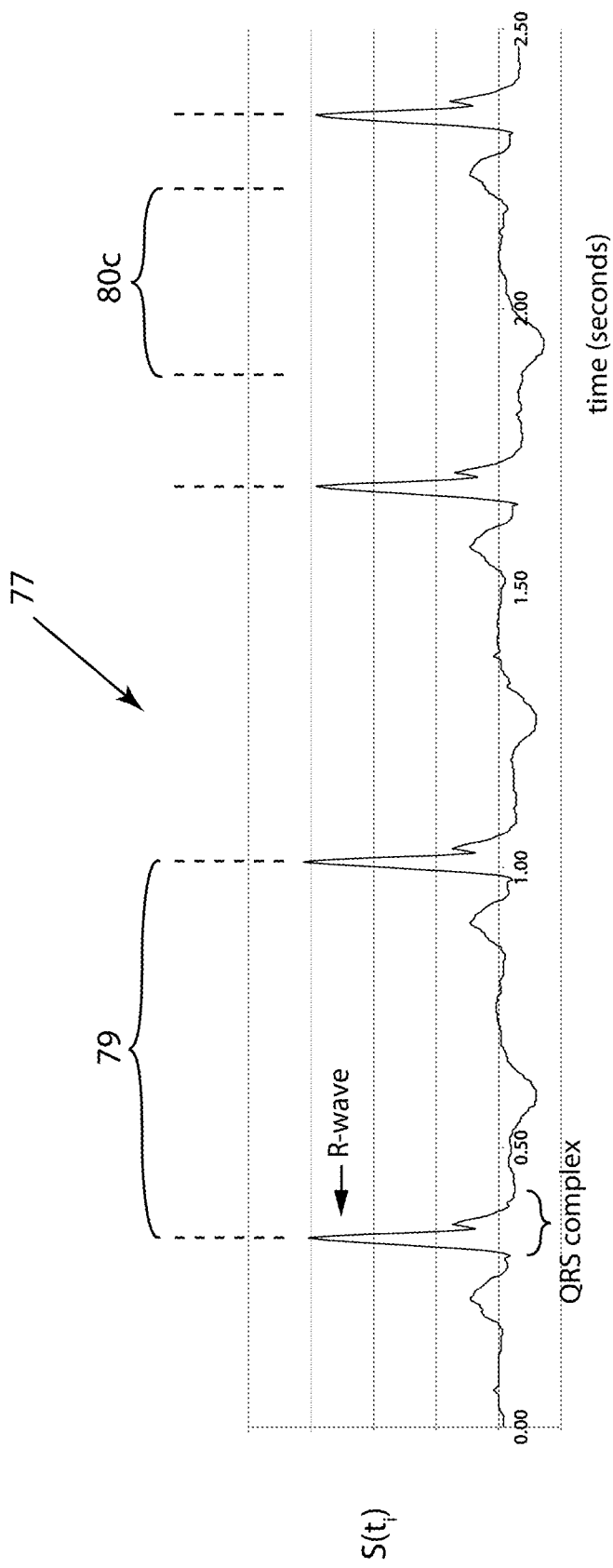
FIG. 6 is an exemplary time plot of a digitized signal $S(t_i)$ from an R-wave detector. The signal is used to derive cardiac phase information for each View 1 and View 2 image.

FIG. 6 is an exemplary time plot 77 of a digitized signal $S(t_i)$ from an R-wave detector. Signal $S(t_i)$ is used to derive cardiac phase information for each View 1 and View 2 image. R-wave intervals 79 are the time periods (cardiac cycle lengths) between neighboring R-waves from the QRS complexes within signal $S(t_i)$. X-ray frames are captured sequentially, each occurring at some time relative to an R-wave interval 79. Then, based on the position in time within R-wave interval 79, a value of cardiac phase is assigned to each View 1 and View 2 image. As mentioned above, it is beneficial to determine 3D cardiac-ablation balloon location using a pair of View 1 and View 2 images taken during periods of minimal cardiac and respiratory motion. As part of this determination in method step 51, a cardiac-phase criterion 80c (as shown in FIG. 6, frames with cardiac phase between 30% and 80% of R-wave interval 79) are frames which satisfy such a cardiac-phase criterion 80c ($0.3 \leq$ cardiac phase $\leq 0.8$). This 30%-80% value of cardiac phase criterion 80c is not intended to be limiting; values outside this range may also be used.

Method steps 43 and 45 (View 1 and View 2, respectively) comprise the identification of location marker 71 as the source of displacement information from which respiratory phase information may be determined. Since motion of objects in the y-direction in a sequence of images (generally parallel to the patient's spine) is primarily the result of respiratory motion, the y-coordinate of an object in a burst (sequence) of images may be used to estimate respiratory phase. In the example which is illustrated below, the smallest y-position value is closest to full exhalation.

It should be noted that in embodiment 30, the most obvious choice of a y-position object referred to in method steps 43 (for View 1) and 45 (for View 2) is radio-opaque location marker 71 (see FIGS. 4-1 and 4-2) of cryoballoon 70, but another radio-opaque object which is moving in the y-direction due to respiration may be used for such y-position measurement. The use of location marker 71 is not intended to be limiting.

The y-coordinate of location marker 71 (also in this example called y-position object 71) is that of the geometric center of y-position object 71, and such determination is well-known to those skilled in image processing. However, the use of the geometric center for such determinations is not intended to be limiting.

Initial identification of y-position object 71 may be done manually on a computer display within the first image in each of the View 1 and View bursts of images. Then the motion of y-position object 71 is determined within each image of the burst in order to determine respiratory phase information for each image in the burst. As in this example, y-position object 71 may be the same object in each of the View 1 and View 2 bursts of images, but it is not necessary that this be so since all that is required is the y-positions within each burst be indicative of the respiratory movement of an object within the burst. The fact that in embodiment 30 the y-position object is the same in both bursts is not intended to be limiting.

Method steps 47 and 49 comprise determination of the respiratory phase of each image in the View 1 and View 2 bursts, respectively. One embodiment of such determination is exemplified in detail in FIGS. 7-1 through 10-2.

Figures 2, 7:
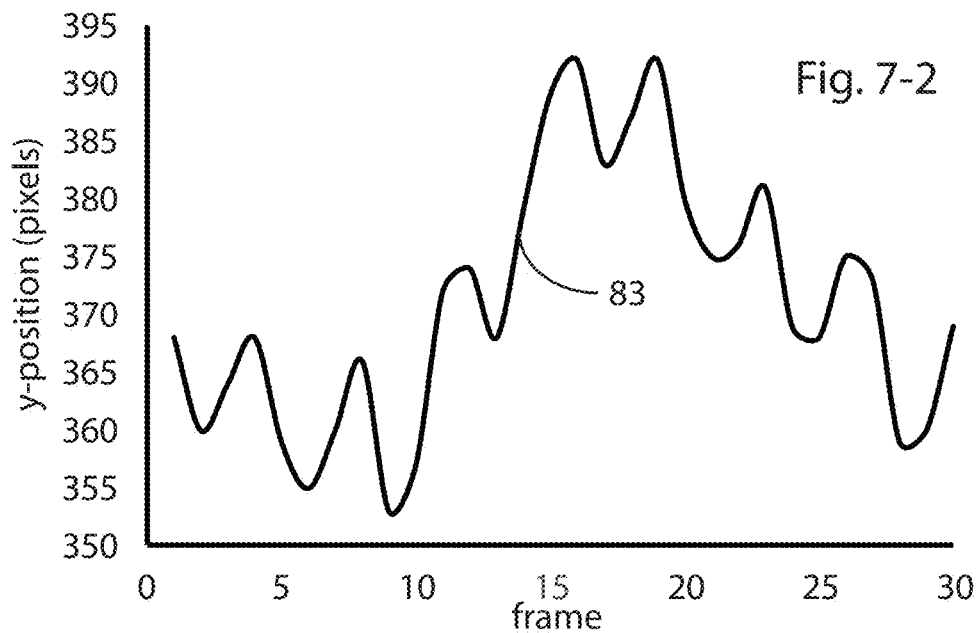
Figures 2, 8:
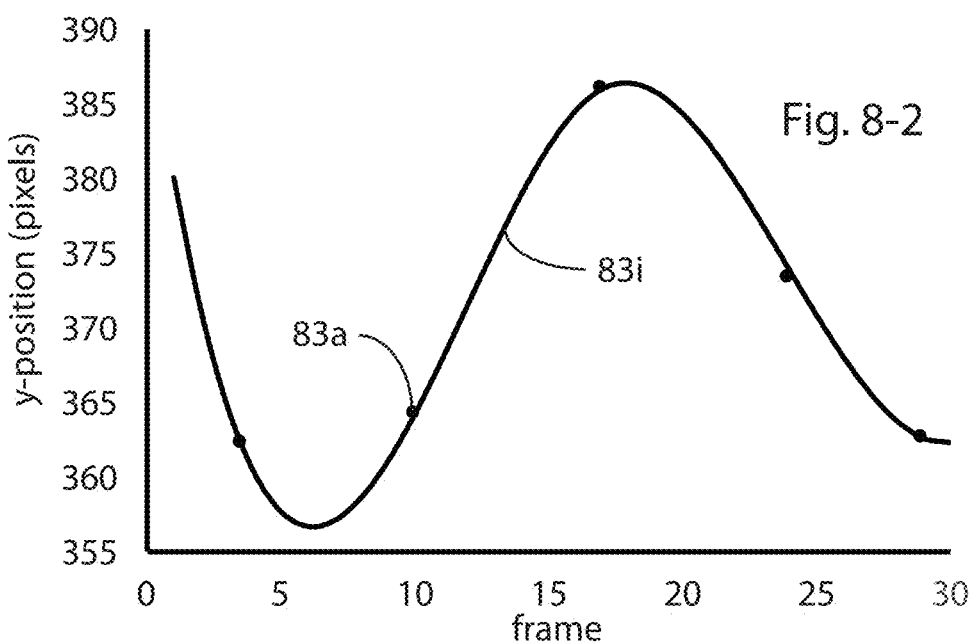
Figure 11:
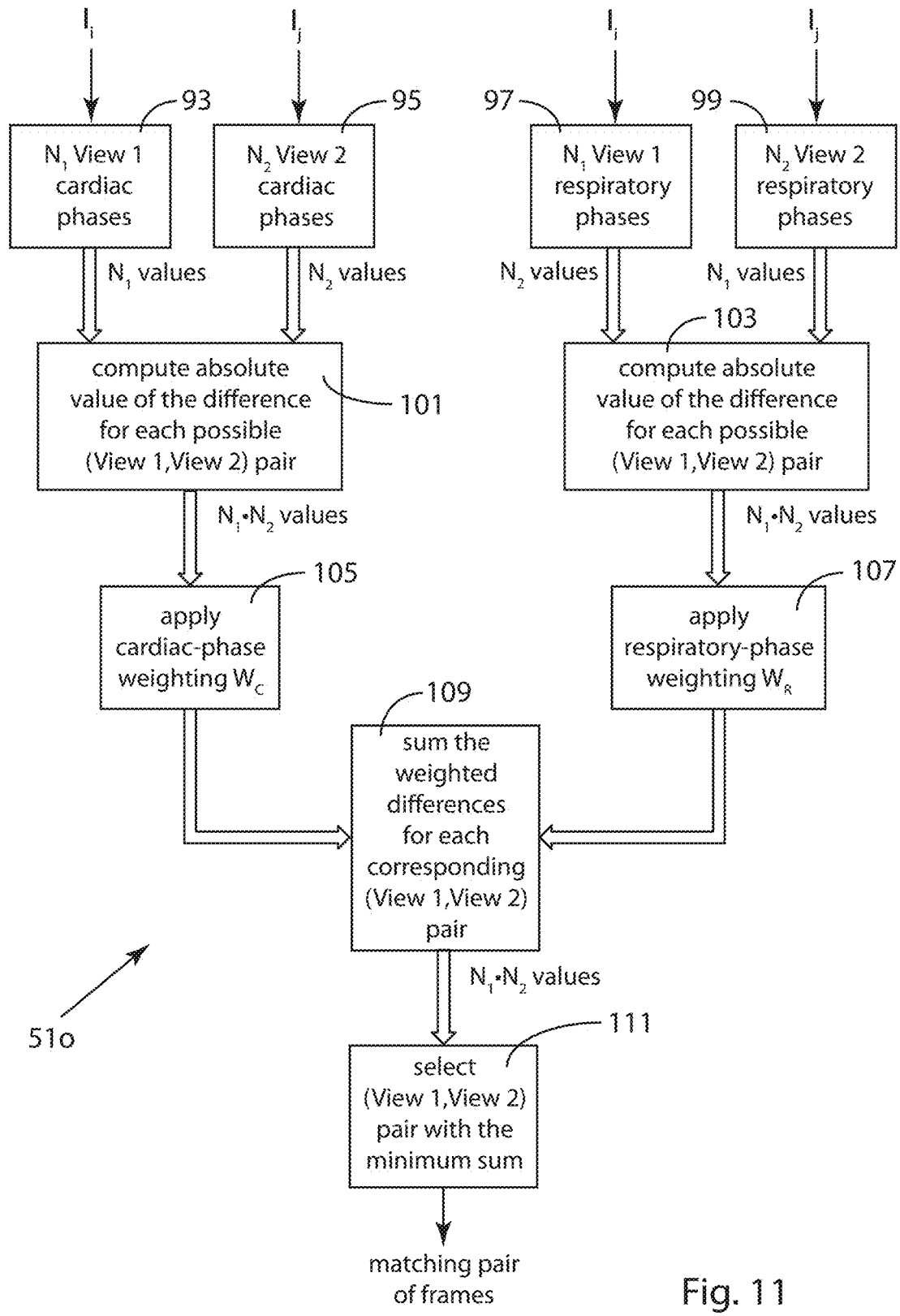
FIG. 11 is a schematic block diagram illustrating an embodiment of the method of selecting the best View 1 and View 2 frames from the sets of candidate View 1 and View 2 frames.

Functional element 51 comprises method steps by which a best View 1 image and a best View 2 image are selected to minimize the effects of cardiac and respiratory motion within the subsequent calculations of the 3D location and orientation of cardiac-ablation balloon 70. One embodiment of method step 51 is illustrated in FIG. 11. As described above, the respiratory phase of View 1 and View 2 images is determined from changes from frame-to-frame in the y-positions of location marker 71 (y-position marker 71) in method steps 47 and 49, respectively. FIGS. 7-1 and 7-2 are plots of exemplary y-position data for y-position marker 71 in the thirty View 1 (data points along line 81) and thirty View 2 (data points along line 83) images, respectively. Given the nature of such data, an estimate of respiratory phase is made, and FIGS. 8-1 and 8-2 are plots of the y-position data of FIGS. 7-1 and 7-2, respectively, which has been smoothed (points 81a and points 83a, respectively) and interpolated (line 81i and line 83i, respectively) to generate an estimate of respiratory phases for View 1 and View 2 images.

Several alternative approaches are possible for such smoothing and interpolation. In this example, each of the View 1 and View 2 frames occurs during some portion of five different R-wave intervals, and each point 81a and 83a is calculated by averaging the y-positions from the frames within each R-wave interval and averaging the corresponding frame numbers to generate highly-smoothed representations of respiratory phase across the View 1 and View 2 sets of frames. Curves 81i and 83i are generated by computing a cubic-spline fit to these sets of points 81a and 83a, respectively, to yield estimates of respiratory phase for each image.

Figures 1, 9:
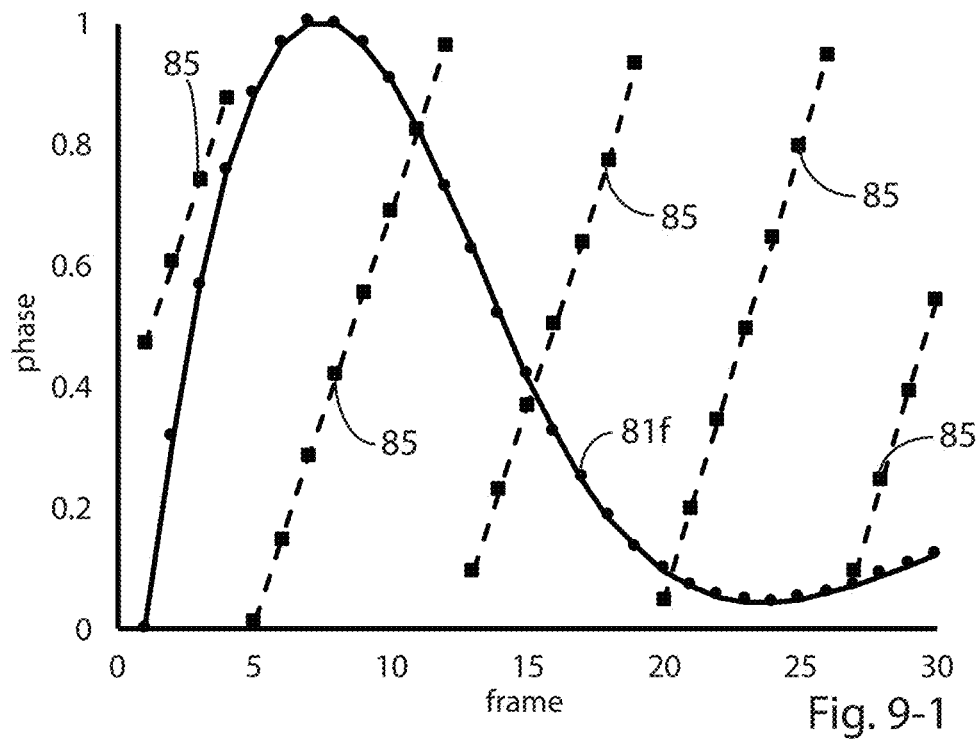

FIGS. 9-1 and 9-2 are plots which present both the respiratory and cardiac phases for each of the thirty View 1 frames and thirty View 2 frames, respectively. The values of both the cardiac phase and respiratory phase have been normalized onto 0-1 scales. In FIGS. 9-1, 9-2, 10-1 and 10-2, cardiac phase values for the frames are shown with small square marks, and respiratory phase values are shown with small circular marks. The solid and dotted lines are shown only for ease of viewing.

In FIGS. 9-1 and 9-2, each dotted-line group of marks 85 (View 1) and 87 (View 2) represent the cardiac phase of frames occurring within a specific R-wave interval 79.

Figures 1, 10:
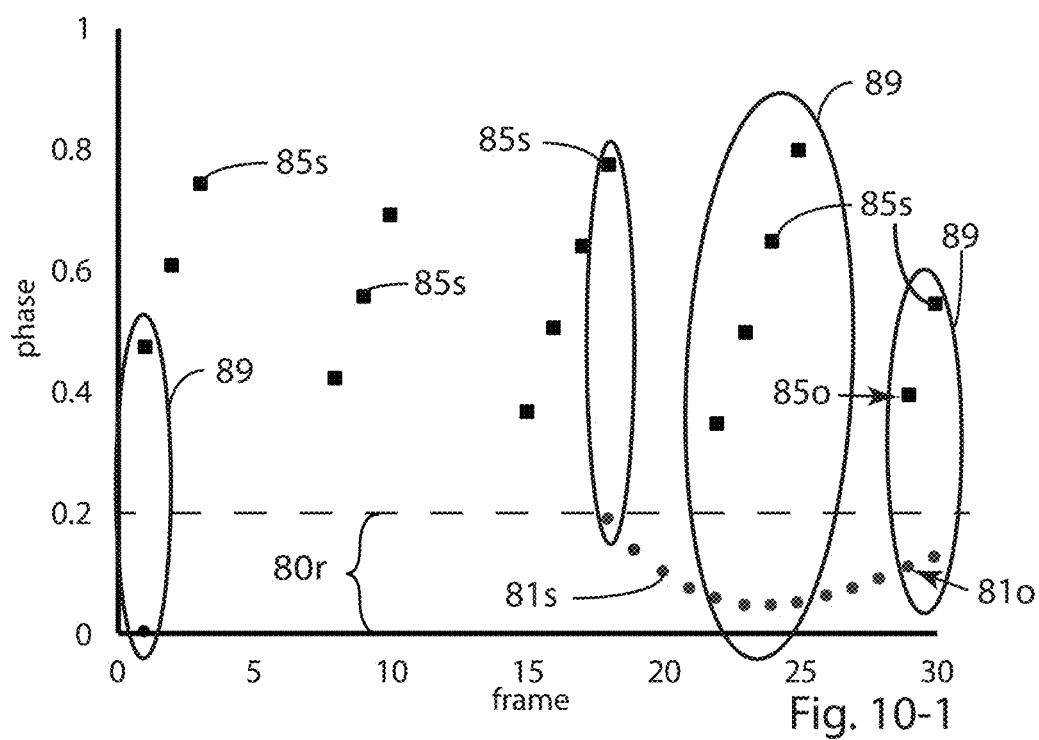
Figures 2, 9:
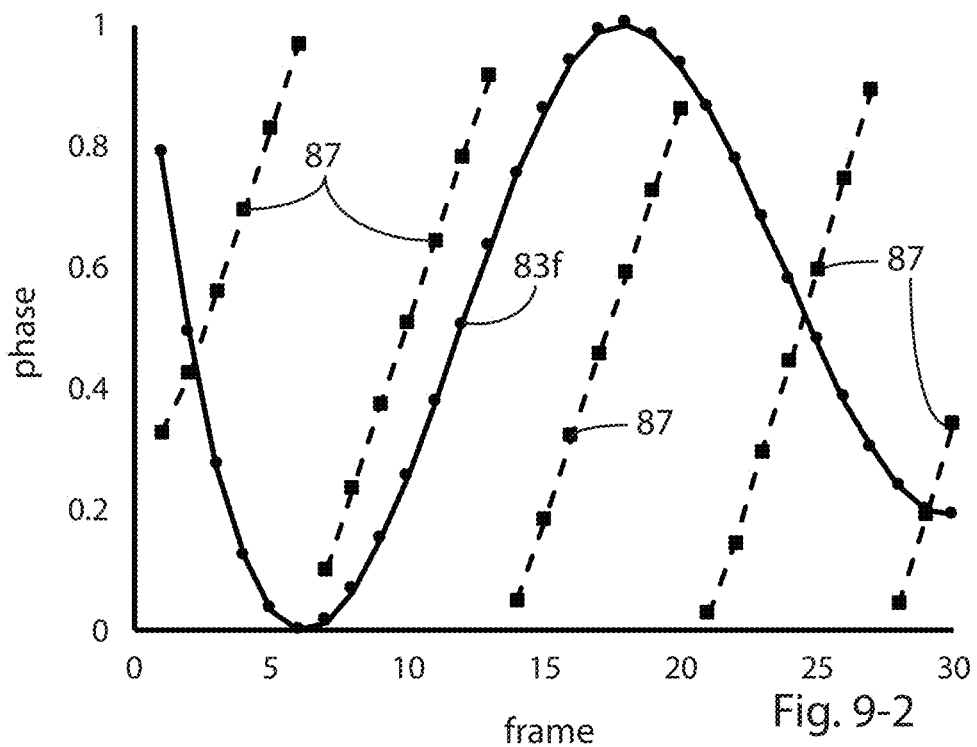
Figures 2, 10:
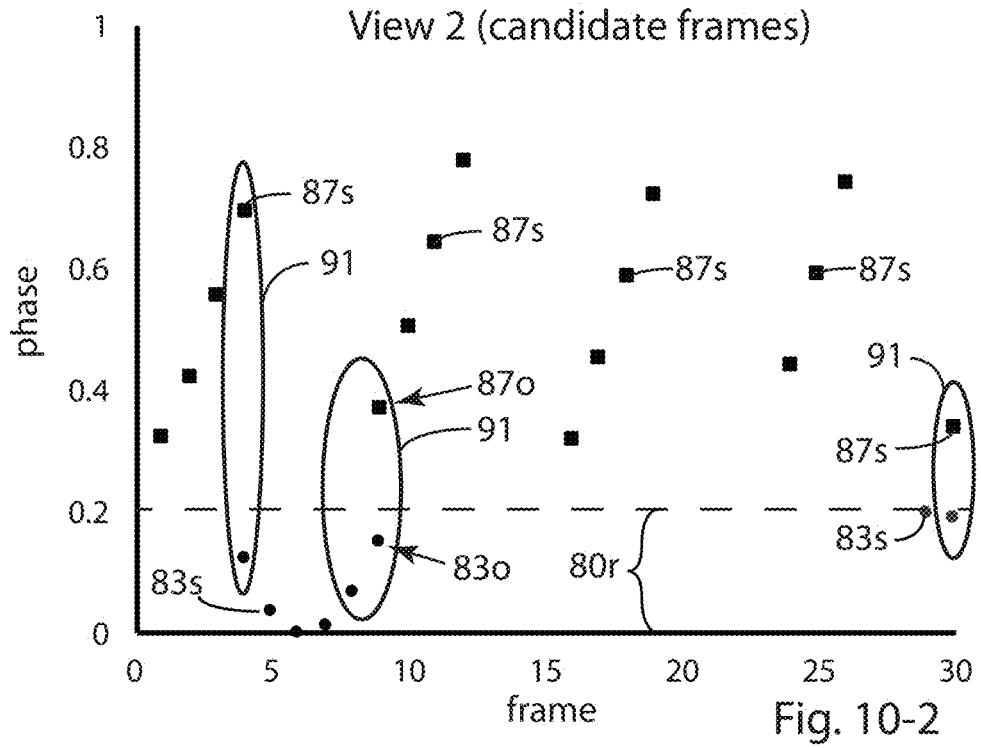

FIG. 10-1 presents plots of View 1 frames 85s which satisfy cardiac-phase criterion 80c and frames 81s which satisfy a respiratory-phase criterion 80r. FIG. 12-2 presents plots of View 2 frames 87s which satisfy cardiac-phase criterion 80c and frames 83s which satisfy respiratory-phase criterion 80r. In this example, the respiratory-phase criterion is such that frames which satisfy the criterion have a respiratory phase between 0% and 20% of maximum exhalation (respiratory phase≤0.2). FIGS. 10-1 and 10-2 therefore show cardiac phase and respiratory phase for a subset of the frames shown in FIGS. 9-1 and 9-2.

Final selection of the best View 1 and View 2 images therefore is reduced to selecting from among the View 1 and View 2 images which satisfy both the cardiac-phase and respiratory-phase criteria. These include View 1 images for which the cardiac phase and respiratory phase values fall within the four regions 89, and View 2 images for which the cardiac phase and respiratory phase values fall within the three regions 91. In this example, the candidate View 1 images are frames 1, 18, 22-25, and 29-30, and the candidate View 2 images $I_j$ are frames 4, 9, and 30.

FIG. 11 is a schematic block diagram illustrating an embodiment 51o of the final selection of the selection of the best View 1 and View 2 frames from the sets of candidate View 1 frames within regions 89 and candidate View 2 frames within regions 91. As indicated in FIG. 11, in this example there are $N_1$ View 1 frames $I_i$ ($N_1$=8; index i=1 to 8) and $N_2$ View frames ($N_2$=4; index j=1 to 4).

In FIG. 11, method steps 93, 95, 97, and 99 represent the fact that calculations within the method steps 51o are made using the cardiac phase and respiratory phase values of View 1 frames $I_i$ and View 2 frames $I_j$ as illustrated in FIGS. 10-1 (View 1) and 10-2 (View 2). In method step 101, the absolute values of the differences between the cardiac phases of all possible pairs of $N_1$ View 1 frames $I_i$ and $N_2$ View 2 frames $I_j$ are computed; there are $N_1 \cdot N_2$ such pairs and absolute difference values. Similarly, in method step 103, $N_1 \cdot N_2$ absolute difference values for the respiratory phases are computed. In functional element 105, each of the $N_1 \cdot N_2$ values cardiac-phase differences is multiplied by cardiac weighting $W_C$, and in similar fashion, in method step 107 the $N_1 \cdot N_2$ respiratory-phase differences are multiplied by respiratory weighting $W_R$. (In the specific example illustrated in FIGS. 7-1 through 10-2, values of $W_C$=1 and $W_R$=1 are used.)

In method step 109, the corresponding pairs of $N_1 \cdot N_2$ cardiac-phase differences and $N_1 \cdot N_2$ respiratory-phase differences are summed to generate a set of $N_1 \cdot N_2$ values, and in method step 111, the minimum value in this set is selected as the "best" or "matching" pair of View 1 and View 2 frames. The weighted sum formed for each pair of frames in method step 109 is one possible measure of the similarity of the View 1 and View 2 frames in each pair of frames, and the similarity criterion is that such measure is to be minimized.

Similarity can be thought of as the reciprocal of this measure since smaller values of such measure represent greater frame-to-frame similarity. In other words, the minimum value of the sum among the $N_1 \cdot N_2$ values computed in method step 109 represents the maximum similarity (minimum combined phase differences) among the pairs of candidate frames. The result of the method steps 51o of FIG. 11 is that View 1 frame number 29 and View 2 frame number 9 are selected as the best or matching pair of frames. In FIG. 10-1, View 1 frame 29 is labeled with reference numbers 81o (cardiac phase) and 85o (respiratory phase). In FIG. 10-2, View 2 frame 9 is labeled with reference numbers 83o (cardiac phase) and 87o (respiratory phase).

Referring again to FIG. 5A and as seen above, the upper portion of the inventive method of embodiment 30 results in the selection of a best (View 1, View 2) pair of images for determining the 3D location and orientation of a cardiac-ablation balloon 70 as shown in FIGS. 4-1 and 4-2. After the best (View 1, View 2) pair of images has been selected in method step 51, in method step 53 a first (or View 1) orientation marker is placed in the selected View 1 image, and a second (or View 2) orientation marker is placed in the selected View 2 image, each at the intersection in the image of the projected surface of balloon 70 and central catheter portion 73 at the farthest point from location marker 71. A user may manually input orientation markers 75-1 and 75-2 using display 14 (or other computer display) and a computer input device (not shown) such as a mouse to position orientation markers 75-1 and 75-2 at the desired intersection point in the selected View 1 and View 2 images.

Preparatory to the determination of the 3D location and orientation of cryoballoon 70, in method element 55, images of location marker 71 in the View 1 and View 2 images are associated with each other as are first and second orientation markers 75-1 and 75-2. The details of these associations are described further with respect to FIGS. 5B and 5C. Images of location marker 71 represent the same physical object of cryoballoon 70. However, first and second orientation markers 75-1 and 75-2 are described herein as two different points since they are in fact placed in the selected View 1 and View 2 images separately, as will be seen below.

Figure 5B:
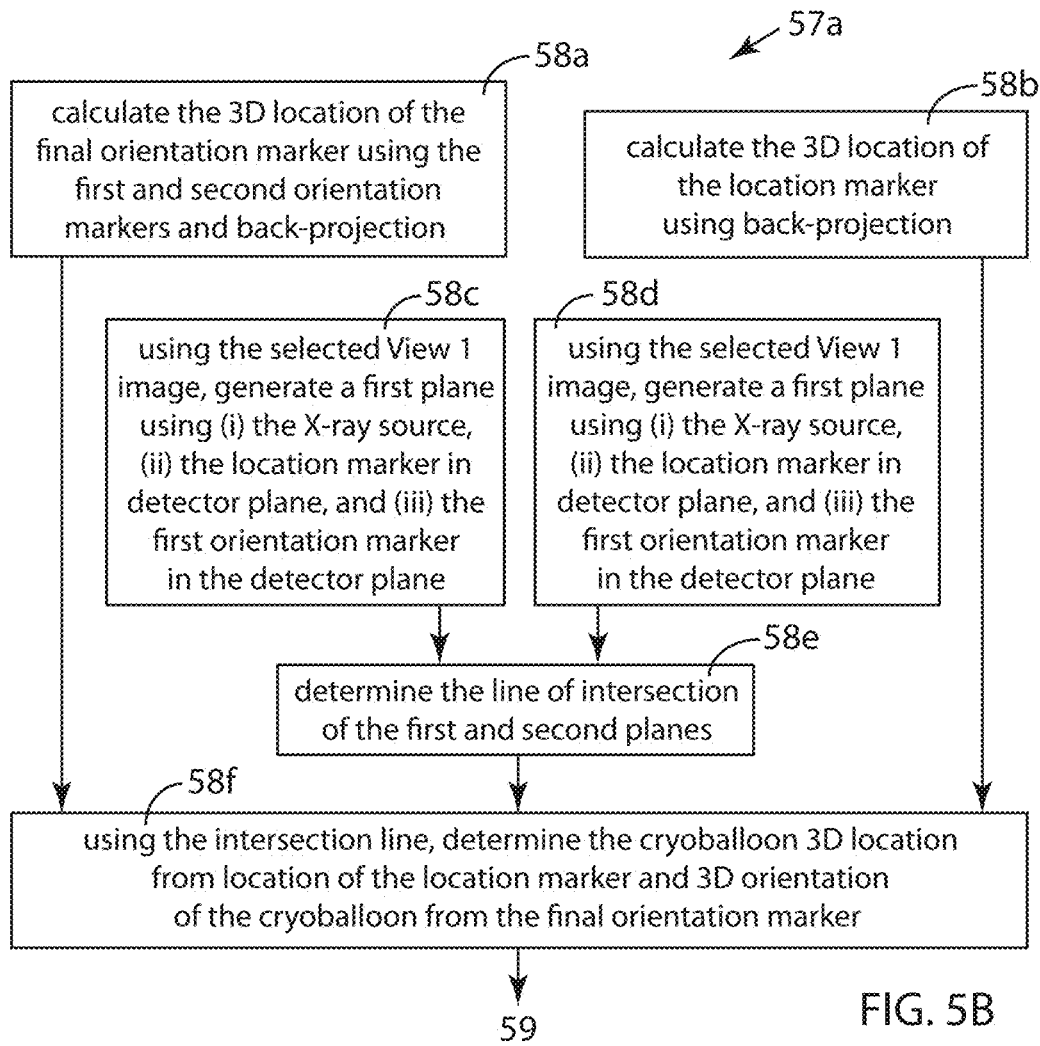
FIG. 5B is a schematic block diagram illustrating one alternative embodiment of the step of determining the 3D location and orientation of the cardiac-ablation balloon in the inventive method of FIG. 5A.
Figure 5C:
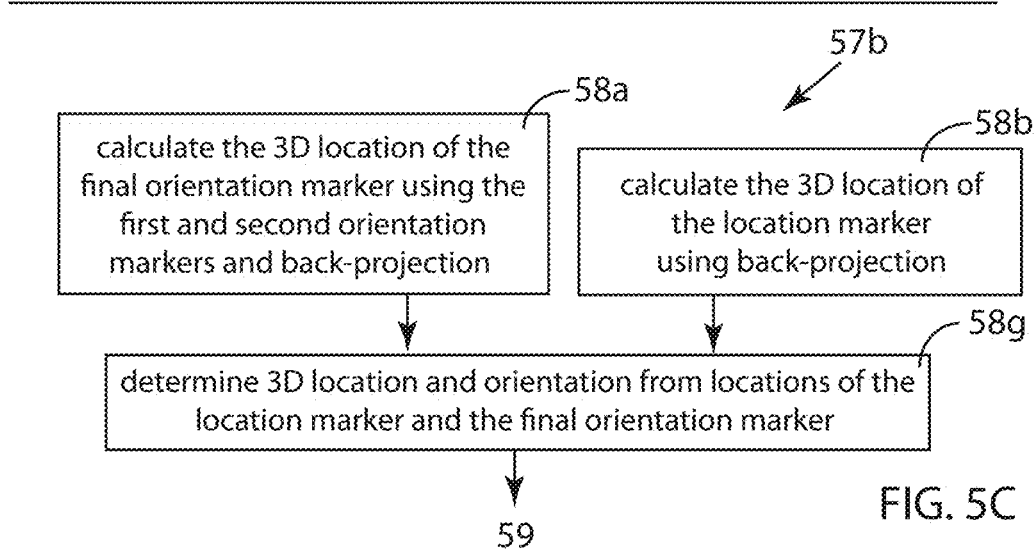
FIG. 5C is a schematic block diagram illustrating a second alternative embodiment of the step of determining the 3D location and orientation of the cardiac-ablation balloon in the inventive method of FIG. 5A.

Embodiment 30 continues to method step 57 in which the 3D location and orientation of cardiac-balloon 70 is determined using View 1 and View 2 locations of location marker 71 and first and second orientation markers 75-1 and 75-2. FIGS. 5B and 5C illustrate two alternative sets (57a and 57b) of method steps for method element 57.

Set 57a of method steps in FIG. 5B is more broadly applicable to the various possible view angles of View 1 and View 2 images while set 57b of method steps in FIG. 5C is useful only when both of the view angles of the View 1 and View 2 images are such that central catheter portion 73 is close to being parallel to table 12. Only in such a case is the assumption that the first and second orientation markers 75-1 and 75-2 are coincident a reasonably accurate assumption, i.e., the two orientation markers 75-1 and 75-2 reasonably represent the same physical point on cryoballoon 70.

Referring now to FIG. 5B, in method element 58a, the 3D location of a final orientation marker is calculated under the assumption that the first and second markers are coincident and using back-projection methods well-known to those skilled in mathematics. Note that the accuracy of this assumption is not critical to set 57a of method steps. In method element 58b, the 3D location of location marker 71 is calculated using back-projection methods.

In method element 58c, a first plane containing three points is generated, these three points being (1) the center of X-ray source 11, (2) location marker 71 in the View 1 image in the plane of detector 13, and (3) first orientation marker 75-1 in the plane of detector 13. In method element 58d, a second plane containing three points is generated, these three points being (1) the center of X-ray source 11, (2) location marker 71 in the View 2 image in the plane of detector 13, and (3) second orientation marker 75-2 in the plane of detector 13. Both of these sets of three points are known with reasonable accuracy. Then in method step 58e, a line of intersection of the first and second planes is computed. All of the calculations necessary for representing the planes and line of intersection are well known to those skilled in mathematics.

In method element 58f, the 3D location of cryoballoon 70 is thus determined from the information provided by method steps 58a-58e. Since location marker 71 is in both first and second planes, it lies along the line of intersection. Since location marker 71 and first and second orientation markers 75-1 and 75-2 are all on central catheter portion 73, then cryoballoon 70 is centered around the line of intersection. And finally, the 3D location of the final orientation marker as calculated in method step 58a is used for is to indicate in which of the two possible orientations along the line of intersection cryoballoon 70 is aligned.

Referring now to set 57b of method steps in FIG. 5C, method elements 58a and 58b contribute the same information as in FIG. 5B. In this case, as described above, when both View 1 and View 2 images are such that central catheter portion 73 lies close to the plane of table 12, then the final orientation marker calculated in method step 58a is a reasonable representation of the 3D location of the end of cryoballoon 70 opposite to location marker 71 and the 3D location and orientation of cryoballoon 70 are thus determined.

Referring again to FIG. 5A, in method step 59, a 3D model of cryoballoon 70 is inserted into the predefined 3D space according to the 3D location and orientation determined in method step 57, and in method step 61, the visualization provided by this insertion is displayed on display 14 or other computer display.

Figure 15B:
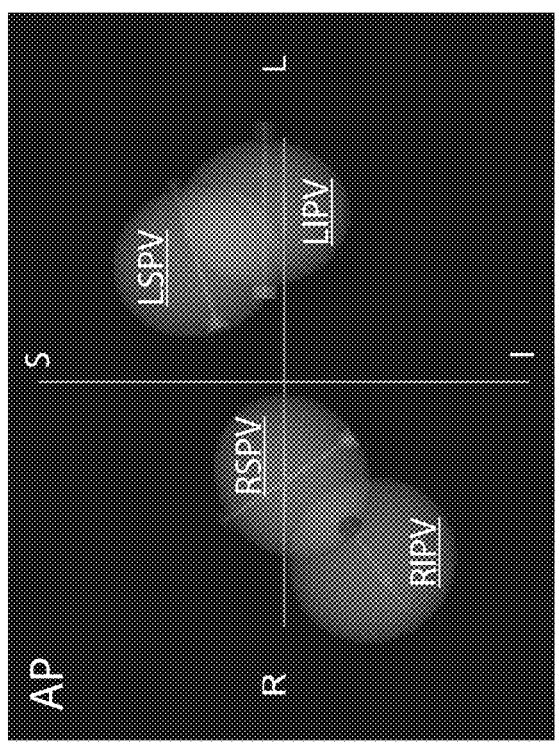
FIGS. 15A and 15B are the same as FIGS. 14A and 14B, respectively, except that the opacity of the 3D perspective image of FIG. 15A has been reduced to enhance the visualization.
Figure 15A:
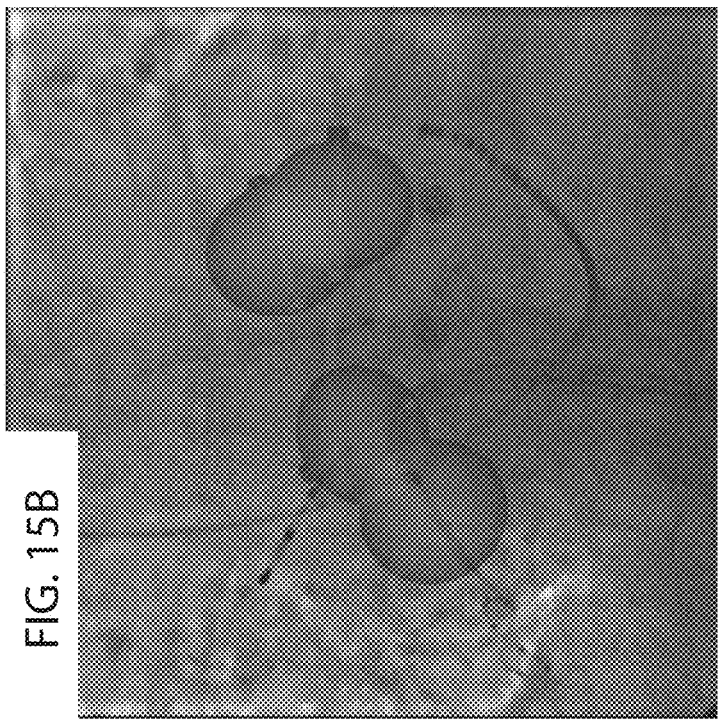

FIGS. 12A through 15B are exemplary images of the display of the visualizations generated by embodiment 30 of the inventive method. FIGS. 12A, 13A-14A, and 15A are computer-generated 3D perspective views of one or more 3D cryoballoon models which have been inserted into the predefined 3D space of fluoroscopic system 10, and FIGS. 12B, 14B and 15B are X-ray images on which such a 3D perspective image has been placed as an overlay. The image of each 3D cryoballoon model in the 3D perspective figures (FIGS. 12A, 13A-14A, and 15A) is labeled with an indication of the medically-pertinent position of cryoballoon 70 within the heart while ablation was applied. These indications are as follows: RSPV=right superior pulmonary vein; RIPV=right inferior pulmonary vein; LSPV=left superior pulmonary vein; and LIPV=left inferior pulmonary vein. (These indications are also used herein to provide reference to the 3D balloon models on which they are marked.) The orientation of the visualization being displayed is also indicated as follows: P=posterior (back of patient); A=anterior (front of patient); R=right side of patient; L=left side pf patient; S=superior (head-end of patient); and I=inferior (foot-end of patient). The view descriptors are also indicated, as follows: AP=anterior/posterior; LL=left lateral; RL=right lateral; and Roof view is from above the patient, parallel to the spine. Finally, the axes lines in these figures further indicate orientation but not necessarily the origin of the predefined 3D workspace of fluoroscopic system 10.

The X-ray images in 12B, 14B and 15B, which include overlay images, do not include the markings indicating medically-pertinent positions of balloon 70, but these positions match the positions indicated in the corresponding 3D perspective views.

Figure 12A:
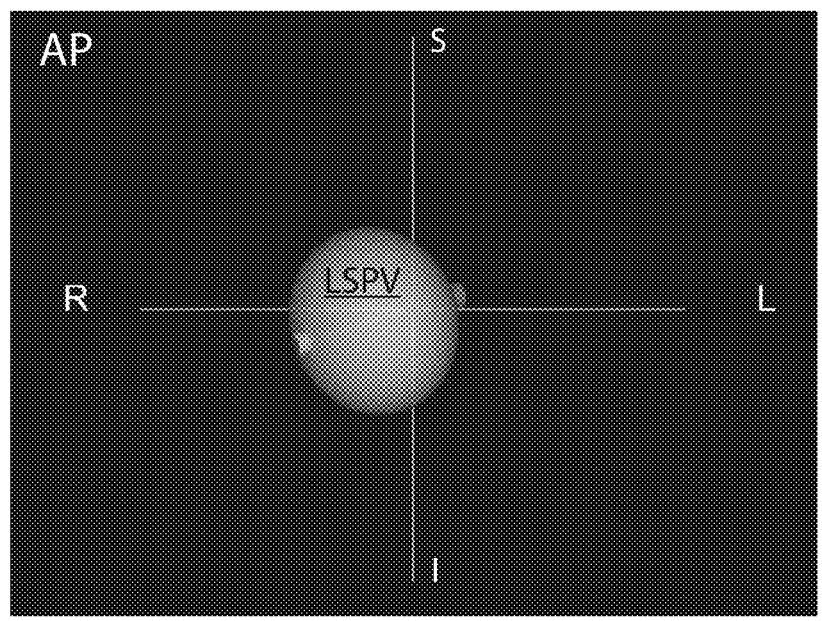
FIG. 12A is a 3D perspective visualization of 3D model of a cryoballoon in a region of a living heart as determined in the example presented herein.
Figure 12B:
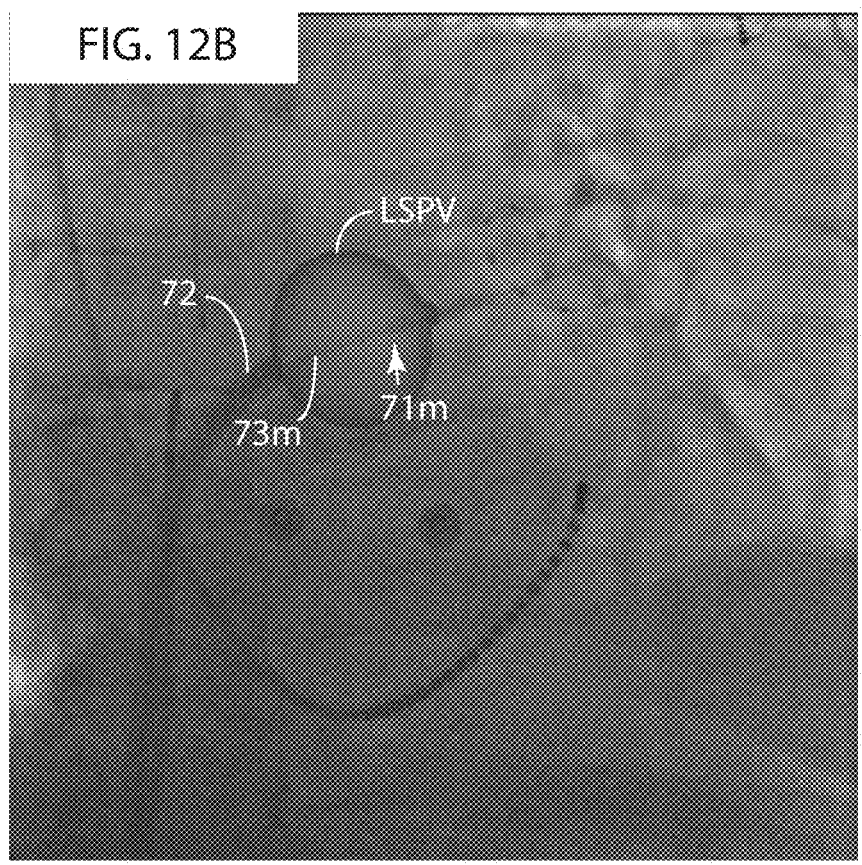
FIG. 12B is a representative X-ray image with an overlay of the 3D model of the cryoballoon of FIG. 12A. The opacity of the overlay is less than 100% to enhance the visualization. The X-ray portion of FIG. 12B is the same as the View 1 image in FIG. 4-1.

FIG. 12A is a 3D perspective visualization of a 3D model LSPV of cryoballoon 70 in a region of a living heart as determined in the example presented herein. FIG. 12B is the View 1 X-ray image of FIG. 4-1 with an overlay of 3D model 70m of FIG. 12A. The opacity of the overlay is less than 100% to enhance the visualization. Because the opacity is less than 100%, the "inside" of 3D balloon model LSPV can be seen to include a location marker 71*m* and a central catheter portion 73*m*.

Figure 13A:
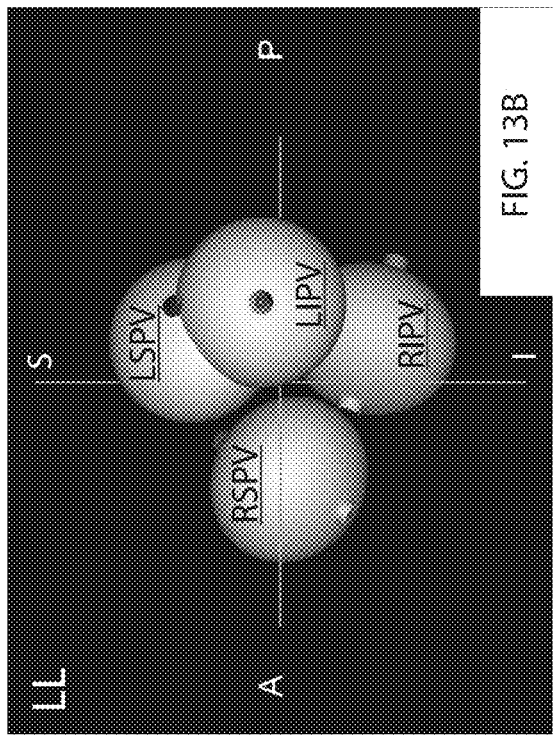
FIG. 13A is a 3D perspective visualization of four 3D models of a cryoballoon which has applied ablation at four positions, one after another, within a living heart. The first ablation was applied at the position indicated in FIG. 12A.
Figure 13B:
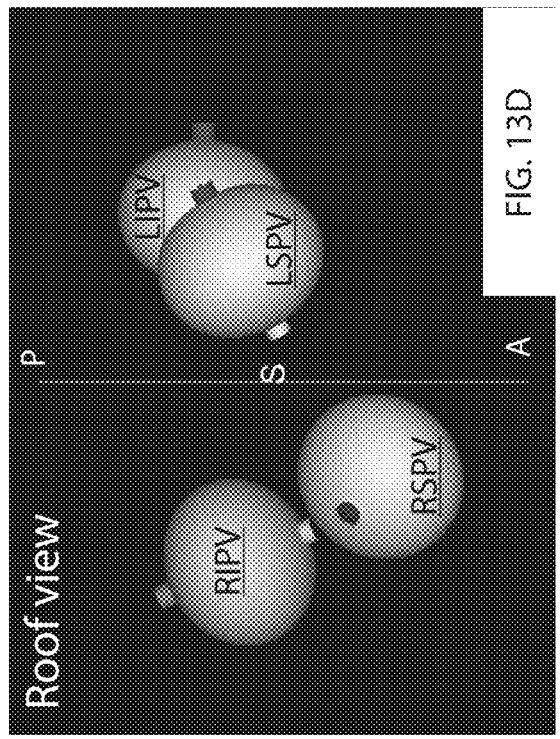
FIG. 13B is a second 3D perspective view of the four 3D balloon models of FIG. 13A.
Figure 13C:
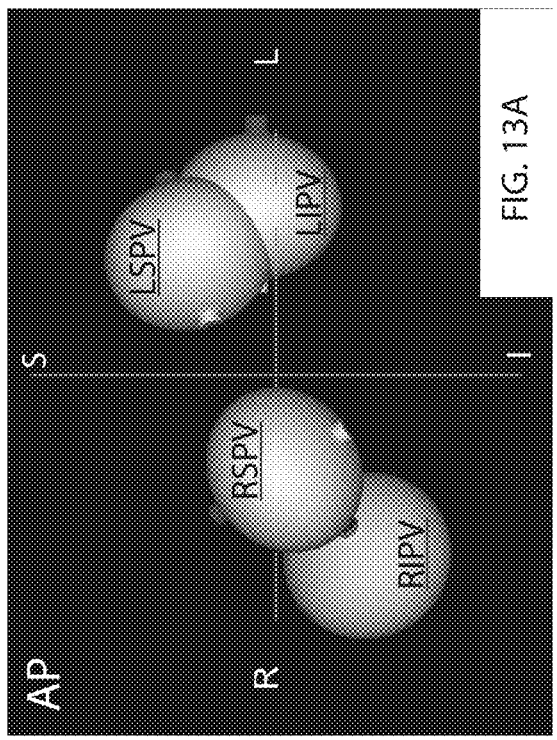
FIG. 13C is a third 3D perspective view of the four 3D balloon models of FIG. 13A.
Figure 13D:
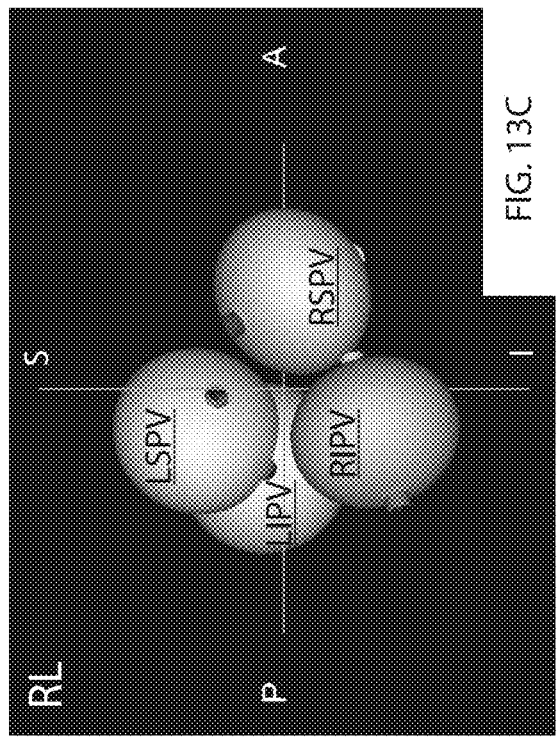
FIG. 13D is a fourth 3D perspective view of the four 3D balloon models of FIG. 13A.

The insertion of the 3D model LSPV of cryoballoon 70 into the predefined 3D space as shown in FIGS. 12A and 12B resulted from the example described above for a first ablation procedure which eventually included ablation of the entrances to all four pulmonary veins. FIG. 13A is a 3D perspective visualization of four 3D models (RSPV, RIPV, LSPV, and LIPV) of cryoballoon 70 at positions in which ablation has been applied, one after another, within a living heart. FIG. 13A shows an anterior/posterior view; FIG. 13B, a left lateral view; FIG. 13C, a right lateral view; and FIG. 13D, a roof view.

With a patient lying on table 12 within fluoroscopic system 10, there may be other sources of motion which affect the accuracy of the determination of the 3D location and orientation of cryoballoon 70. Among these are patient movement relative to table 12 (other than cardiac and respiratory motion), adjustments to the position of table 12, and adjustments to the orientations of base 7, C-arm 8, and L-arm 9. The latter two of these sources of motion are compensated for by virtue of fluoroscopic system 10 having control subsystems (not shown) commanded via control panel 15 which provide measurements of the amount of translation and rotation which has occurred, and the information is provided to method embodiment 30 to enable the coordinate system to be transformed accordingly.

However, patient motion relative to table 12 must be compensated for using other methods. One such method employs at least two external markers on the patient which are initially 3D-located during the inventive View 1/View 2 procedure described herein. Two such markers 76 are indicated in FIGS. 4-1 and 4-2 and also visible in FIGS. 12B, 14B, and 15B. After such initialization, the 2D x,y positions of external markers 76 are monitored within the single-plane X-ray images of the patient, and the sensed x,y motion of the patient is used to transform the coordinate system accordingly. Patient motion (translational or rotational motion) which is significantly out of the x,y plane cannot be compensated for, but such patient movement is not encountered too frequently during such procedures.

FIGS. 14B and 15B are images which resulted from a translation of table 12. (FIG. 14A is the same anterior/posterior view as FIG. 13A, placed next to FIG. 14B for convenience in identifying objects in FIG. 14B.) FIG. 14B is a representative X-ray image on which an overlay of the 3D perspective image of FIG. 14A has been placed. The opacity of the 3D cryoballoon models (RSPV, RIPV, LSPV, and LIPV) of cryoballoon 70 in the overlay image is 100%; therefore, in this case, none of the detail behind such models in the X-ray image is visible. As alluded to above, the X-ray image in FIG. 14B is slightly different from the X-ray image of FIG. 4-1; the X-ray image was taken after all four ablation positions were achieved and after table 12 of fluoroscopic system 10 had been translated to the right. (As noted above, the markings have not been added to FIG. 14B; such indications are those made in FIG. 14A.)

The process of cardiac ablation consumes a modest amount time, i.e., the time required for the ablation process to achieve its intended effect on the cardiac tissue. Consequently, all of the method steps which occur after placing, inflating, and positioning cardiac ablation balloon 70 do not add time to the medical procedure which the patient is undergoing.

The example ablation procedure described above involves ablations at the antrums of the pulmonary veins. As can be easily seen, the inventive method can also be advantageously applied in other areas of the heart where ablation may be required. The antrum ablation locations of the example are not intended to be limiting.

While the principles of this invention have been described in connection with specific embodiments, it should be understood clearly that these descriptions are made only by way of example and are not intended to limit the scope of the invention.

The invention claimed is:

1. A method for generating and displaying a 3D visualization of a cardiac-ablation balloon in a region of a living heart within a predefined 3D space, the method using single-plane fluoroscopic images and comprising:

placing, inflating and positioning the balloon into the region, the balloon having a radio-opaque location marker and central catheter portion;

capturing a burst of first-view digitized 2D images of the region from a fluoroscope positioned at a first angle;

capturing a burst of second-view digitized 2D images of the region from the fluoroscope positioned at a second angle different from the first angle;

selecting first-view and second-view images from the bursts such that the difference between measures of cardio-respiratory phases of the selected first-view and second-view images is minimized;

identifying the location marker in each of the two selected images;

placing first and second orientation markers in the selected first-view and second-view images, respectively, where the central catheter portion intersects a projected image of the inflated balloon at the farthest point from the location marker;

associating the location marker and the second orientation marker in the selected second-view image with the location marker and the first orientation marker in the selected first-view image;

determining 3D location and orientation of the balloon in the region using the selected first-view and second-view images; and the associated first and second orientation markers based on the determined location and orientation, inserting a 3D balloon model into the predefined space to generate the 3D visualization; and displaying the 3D visualization on a display device, whereby a user can visualize where cardiac ablation was applied within the region after the balloon has been moved from where the ablation occurred.

2. The method of claim 1 wherein the cardiac ablation balloon uses light energy to ablate cardiac tissue.

3. The method of claim 1 wherein the balloon uses radio-frequency energy to ablate cardiac tissue.

4. The method of claim 1 wherein the balloon uses focused ultrasonic energy to ablate cardiac tissue.

5. The method of claim 1 wherein the balloon is a cryoballoon using freezing to ablate cardiac tissue.

6. The method of claim 1 wherein the displaying step includes displaying the projected image of the 3D visualization onto a 2D fluoroscopic image of the region.

7. The method of claim 1 wherein the displaying step includes displaying the 3D visualization in 3D rotatable perspective format.

8. The method of claim 1 wherein selecting a first-view image and a second-view image includes determining a cardiac phase and a respiratory phase for each captured first-view and second-view image.

9. The method of claim 8 wherein selecting the first-view and second-view images includes the steps of:
  identifying candidate images in the first and second bursts of images for which a cardiac-phase criterion and a respiratory-phase criterion are satisfied; and
  selecting the first-view image and the second-view image from the candidate images using a similarity criterion based on the cardiac phase and respiratory phase of the candidate images.

10. The method of claim 9 wherein the selecting step further includes:
  for each pair of a candidate first-view image $I_i$ and a candidate second-view image $I_j$, computing the sum of the absolute value of the difference between the cardiac phases of images $I_i$ and $I_j$ and the absolute value of the difference between the respiratory phases of images $I_i$ and $I_j$; and
  selecting the pair of first-view and second-view images for which the sum is the minimum.

11. The method of claim 10 wherein the cardiac-phase difference and respiratory-phase difference are given relative weights prior to summing.

12. The method of claim 8 wherein the cardiac phase of each image is estimated using an R-wave detector to identify R-waves and measure R-wave intervals.

13. The method of claim 12 wherein selecting the first-view and second-view images includes the steps of:
  identifying candidate images in the first and second bursts of images for which a cardiac-phase criterion and a respiratory-phase criterion are satisfied; and
  selecting the first-view image and the second-view image from the candidate images using a similarity criterion based on the cardiac phase and respiratory phase of the candidate images.

14. The method of claim 13 wherein the estimate of the cardiac phase of an image is the percentage of time, along the R-wave interval, at which such image was captured.

15. The method of claim 14 wherein the cardiac-phase criterion is satisfied if the estimated cardiac phase of an image is between 30% and 80%.

16. The method of claim 8 wherein the respiratory phase of each image in a burst of images is estimated by:
  determining an exhalation/inhalation range from the location of a radio-opaque object in the images of the burst; and
  determining the percentage along the exhalation/inhalation range of the location of the radio-opaque object in such image.

17. The method of claim 16 wherein the radio-opaque object is the location marker.

18. The method of claim 17 wherein selecting the first-view and second-view images includes the steps of:
  identifying candidate images in the first and second bursts of images for which a cardiac-phase criterion and a respiratory-phase criterion are satisfied; and
  selecting the first-view image and the second-view image from the candidate images using a similarity criterion based on the cardiac phase and respiratory phase of the candidate images.

19. The method of claim 18 wherein the respiratory-phase criterion is satisfied when the respiratory phase of an image is between 0% and 20% of maximum exhalation.

20. The method of claim 1 wherein all but the placing, inflating and positioning step takes place during the cardiac ablation.

21. The method of claim 1 wherein determining the 3D location and orientation of the cardiac-ablation balloon includes determining the 3D locations of the location marker and a final orientation marker from the selected first-view and second-view images using back-projection calculations.

22. The method of claim 21 wherein the fluoroscope includes a detector defining a detector plane and an X-ray source defining a source point, and determining the 3D location and orientation of the cardiac-ablation balloon further comprises:
  generating a first plane containing three points defined by:
    the location marker and the first orientation marker of the selected first-view image in the detector plane; and
    the source point;
  generating a second plane containing three points defined by:
    the location marker and the selected second orientation marker of the second-view image in the detector plane; and
    the source point;
  determining the line of intersection of the first and second planes;
  determining the location of the balloon from the 3D location of the location marker on the line of intersection; and
  determining the orientation of the balloon from the determined 3D location of the final orientation marker.

23. A method for generating and displaying a 3D visualization of a cardiac-ablation balloon in a region of a living heart within a predefined 3D space, the method using single-plane fluoroscopic images and comprising:
  placing, inflating and positioning the balloon, the balloon having a radio-opaque location marker and a radio-opaque central catheter portion;
  capturing a first-view digitized 2D image of the region from a first fluoroscope positioned at a first angle;
  capturing a second-view digitized 2D image of the region from a second fluoroscope positioned at a second angle different from the first angle;
  identifying the location marker in each image;
  placing first and second orientation markers in the first-view and second-view images, respectively, where the central catheter portion intersects a projected image of the inflated balloon at the farthest point from the location marker;
  associating the location marker and second orientation marker in the second-view image with the location marker and first orientation marker in the first-view image;
  determining 3D location and orientation of the balloon in the region using the first-view and second-view images; and the associated first and second orientation markers
  based on the determined location and orientation, inserting a 3D balloon model into the predefined space to generate the 3D visualization; and
  displaying the 3D visualization on a display device,
  whereby a user can visualize where cardiac ablation was applied within the region after the balloon has been moved from where the ablation occurred.

24. The method of claim 23 wherein:
  capturing the first-view image includes capturing a first burst of images and selecting the first-view image from among the first burst of images; and
  capturing the second-view image includes capturing a second burst of images and selecting the second-view image from among the second burst of images.

25. The method of claim 24 further including determining a cardiac phase and a respiratory phase for each captured first-view and second-view image.

26. The method of claim 25 wherein selecting the first-view and second-view images includes the steps of:
identifying candidate images in the first and second bursts of images for which a cardiac-phase criterion and a respiratory-phase criterion are satisfied; and
selecting the first-view image and the second-view image from the candidate images using a similarity criterion based on the cardiac phase and respiratory phase of the candidate images.

27. The method of claim 23 wherein determining the 3D location and orientation of the cardiac-ablation balloon includes determining the 3D locations of the location marker and a final orientation marker from the first-view and second-view images using back-projection calculations.

28. The method of claim 27 wherein the fluoroscopes include a detector defining a detector plane and an X-ray source defining a source point, and determining the 3D location and orientation of the cardiac-ablation balloon further comprises:
generating a first plane containing three points defined by:
the location marker and the first orientation marker of the first-view image in the detector plane; and
the source point;
generating a second plane containing three points defined by:
the location marker and the second orientation marker of the second-view image in the detector plane; and
the source point;
determining the line of intersection of the first and second planes;
determining the location of the balloon from the 3D location of the location marker on the line of intersection; and
determining the orientation of the balloon from the determined 3D location of the final orientation marker.

29. A method for generating and displaying a 3D visualization of a cardiac-ablation balloon in a region of a living heart within a predefined 3D space, the balloon having a radio-opaque location marker and a radio-opaque central-catheter portion, the balloon having been placed, inflated and positioned in the region, the method using single-plane fluoroscopic images and comprising:
capturing a burst of first-view digitized 2D images of the region from a fluoroscope positioned at a first angle;
capturing a burst of second-view digitized 2D images of the region from the fluoroscope positioned at a second angle different from the first angle;
selecting first-view and second-view images from the bursts such that the difference between measures of cardio-respiratory phases of the selected first-view and second-view images is minimized;
identifying the location marker in each of the two selected images;
placing first and second orientation markers in the selected first-view and second-view images, respectively, where the central catheter portion intersects a projected image of the inflated balloon at the farthest point from the location marker;
associating the location marker and the second orientation marker in the selected second-view image with the location marker and first orientation marker in the selected first-view image;
determining 3D location and orientation of the balloon in the region using the selected first-view and second-view images; and the associated first and second orientation markers;
based on the determined location and orientation, inserting a 3D balloon model into the predefined space to generate the 3D visualization; and
displaying the 3D visualization on a display device,
whereby a user can visualize where cardiac ablation was applied within the region after the balloon has been moved from where the ablation occurred.

30. The method of claim 29 wherein determining the 3D location and orientation of the cardiac-ablation balloon includes determining the 3D locations of the location marker and a final orientation marker from the selected first-view and second-view images using back-projection calculations.

31. The method of claim 30 wherein the fluoroscope includes a detector defining a detector plane and an X-ray source defining a source point, and determining the 3D location and orientation of the cardiac-ablation balloon further comprises:
generating a first plane containing three points defined by:
the location marker and the first orientation marker of the first-view image in the detector plane; and
the source point;
generating a second plane containing three points defined by:
the location marker and the second orientation marker of the second-view image in the detector plane; and
the source point;
determining the line of intersection of the first and second planes;
determining the location of the balloon from the 3D location of the location marker on the line of intersection; and
determining the orientation of the balloon from the determined 3D location of the final orientation marker.

* * * * *